(12) United States Patent
Bowlin et al.

(10) Patent No.: US 10,046,081 B2
(45) Date of Patent: *Aug. 14, 2018

(54) ELECTROSPUN DEXTRAN FIBERS AND DEVICES FORMED THEREFROM

(71) Applicants: Virginia Commonwealth University, Richmond, VA (US); The Henry M. Jackson Foundation for the Advancement of Military Medicine, Inc., Bethesda, MD (US)

(72) Inventors: Gary Bowlin, Mechanicsville, VA (US); David Simpson, Mechanicsville, VA (US); James Bowman, Richmond, VA (US); Stephen Rothwell, Richmond, VA (US)

(73) Assignees: The Henry M Jackson Foundation for the Advancement of Military Medicine, Inc., Rockville, MD (US); Virginia Commonwealth University, Richmond, VA (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/445,566

(22) Filed: Jul. 29, 2014

(65) Prior Publication Data

US 2015/0112287 A1 Apr. 23, 2015
US 2016/0175477 A9 Jun. 23, 2016

Related U.S. Application Data

(63) Continuation of application No. 12/937,322, filed as application No. PCT/US2009/040182 on Apr. 10, 2009, now Pat. No. 9,399,082.

(60) Provisional application No. 61/044,165, filed on Apr. 11, 2008.

(51) Int. Cl.
| *A61L 15/28* | (2006.01) |
| *A61L 15/44* | (2006.01) |
| *A61L 15/32* | (2006.01) |
| *A61L 15/38* | (2006.01) |

(52) U.S. Cl.
CPC ............... *A61L 15/28* (2013.01); *A61L 15/32* (2013.01); *A61L 15/38* (2013.01); *A61L 15/44* (2013.01); *A61L 2300/252* (2013.01); *A61L 2300/254* (2013.01); *A61L 2300/418* (2013.01); *A61L 2400/04* (2013.01); *Y10T 156/10* (2015.01)

(58) Field of Classification Search
CPC ............................... A61L 15/28; Y10T 156/10
See application file for complete search history.

(56) References Cited

U.S. PATENT DOCUMENTS

| 5,447,423 A | 9/1995 | Fuisz et al. |
| 5,773,033 A * | 6/1998 | Cochrum ............... A61K 35/16 424/530 |
| 6,116,880 A | 9/2000 | Bogue et al. |
| 6,762,336 B1 | 7/2004 | MacPhee et al. |
| 6,821,479 B1 | 11/2004 | Smith et al. |
| 7,067,444 B2 | 6/2006 | Luo et al. |
| 7,101,862 B2 | 9/2006 | Cochrum et al. |
| 2004/0193088 A1 | 9/2004 | Looney |
| 2005/0226916 A1* | 10/2005 | Cochrum .......... A61F 13/00034 424/445 |
| 2006/0240110 A1 | 10/2006 | Kiick et al. |
| 2006/0264130 A1 | 11/2006 | Karles et al. |
| 2007/0160653 A1 | 7/2007 | Fisher et al. |
| 2007/0255238 A1 | 11/2007 | Cochrum et al. |
| 2008/0020015 A1 | 1/2008 | Carpenter et al. |
| 2008/0021545 A1 | 10/2008 | Reneker |
| 2008/0265469 A1 | 10/2008 | Li et al. |
| 2009/0053288 A1 | 2/2009 | Eskridge et al. |
| 2009/0177272 A1 | 7/2009 | Abbate et al. |
| 2009/0192214 A1 | 7/2009 | Gravett et al. |
| 2009/0291124 A1 | 11/2009 | Bedard |
| 2010/0100123 A1 | 4/2010 | Benett |
| 2011/0021964 A1 | 1/2011 | Larsen et al. |
| 2011/0071498 A1 | 3/2011 | Hakimimer et al. |
| 2011/0112572 A1 | 5/2011 | Miller |
| 2011/0125089 A1 | 5/2011 | Senderoff et al. |
| 2011/0150973 A1 | 6/2011 | Bowlin et al. |
| 2011/0250257 A1 | 10/2011 | Arthur et al. |

FOREIGN PATENT DOCUMENTS

| JP | 2005290610 A | 10/2005 |
| WO | 2006088912 A2 | 8/2006 |
| WO | WO2006088912 | 8/2006 |

OTHER PUBLICATIONS

Jiang et al, "Optimization and Characterization of Dextran Membranes Prepared by Electrospinning", Biomacromolecules, 5(2):326-333 (Mar.-Apr. 2004).
Jiang et al., "Modulation of Protein Release from Biodegradable Core—Shell Structured Fibers Prepared by Coaxial Electrospinning", Journal of Biomedical Materials Research Part B: Applied Biomaterials, 79B(1):50-57 (Oct. 2006).
Notification of Transmittal of The International Search Report and the Written Opinion of the International Searching Authority, or the Declaration (PCT/12/60643) dated Dec. 20, 2012 (10 pages).
Stephen Rothwell et. al., A Salmon Thrombin-Fibrin Bandage Controls Arterial Bleeding in a Swine Aortotomy Model, The Journal of Trauma Injury, Infection and Critical Care, 2005-vol. 59, No. 1, pp. 143-149.
Notification of First Office Action, CA 2,721,162 (PCT US2009040182) Aug. 27, 2015, 3 pages.

* cited by examiner

*Primary Examiner* — Dennis J Parad
(74) *Attorney, Agent, or Firm* — Moss & Barnett; Michael A. Bondi

(57) ABSTRACT

The invention generally relates to dextran fibers which are preferably electrospun and devices formed from such fibers. In particular, such devices may include substances of interest (such as therapeutic substances) associated with the electrospun fibers. Upon exposure to a liquid the electrospun fibers dissolve immediately and the substances of interest are released into the liquid. Exemplary devices include bandages formed from electrospun dextran fibers and associated agents that promote hemostasis, such as thrombin and fibrinogen.

10 Claims, 14 Drawing Sheets

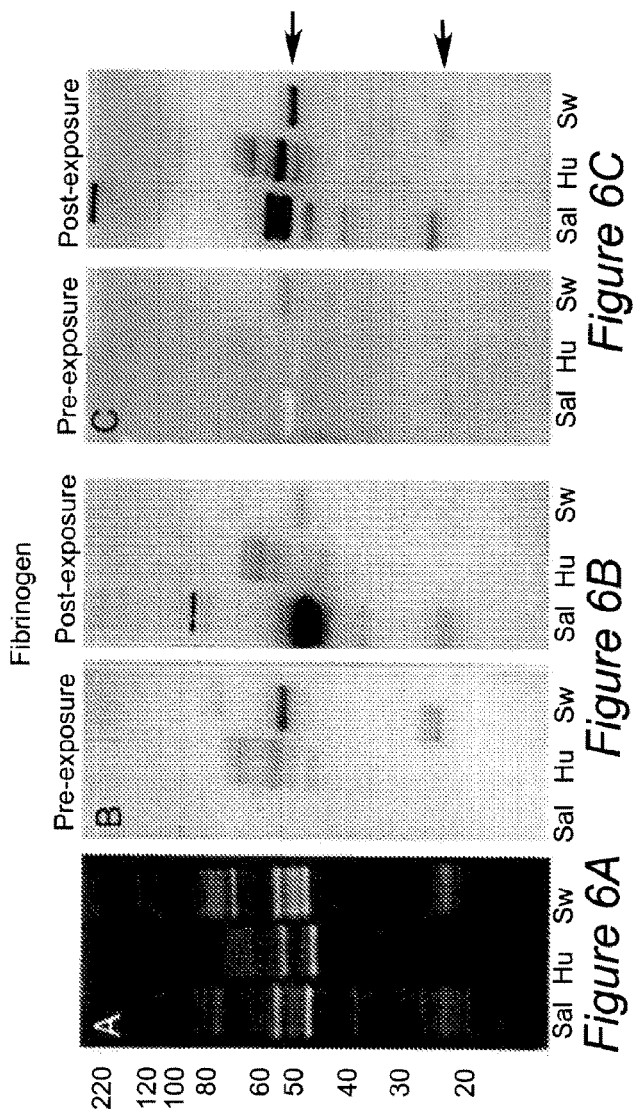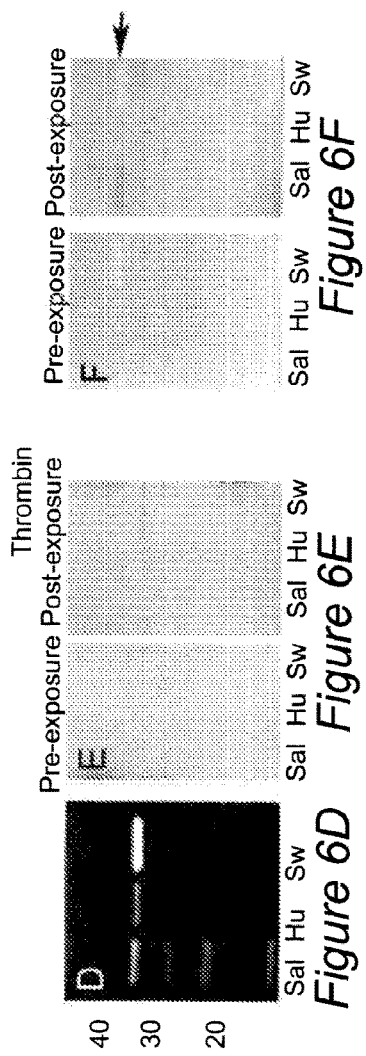

ELECTROSPUN DEXTRAN FIBERS AND DEVICES FORMED THEREFROM

REFERENCE TO RELATED APPLICATION

Figure 1:
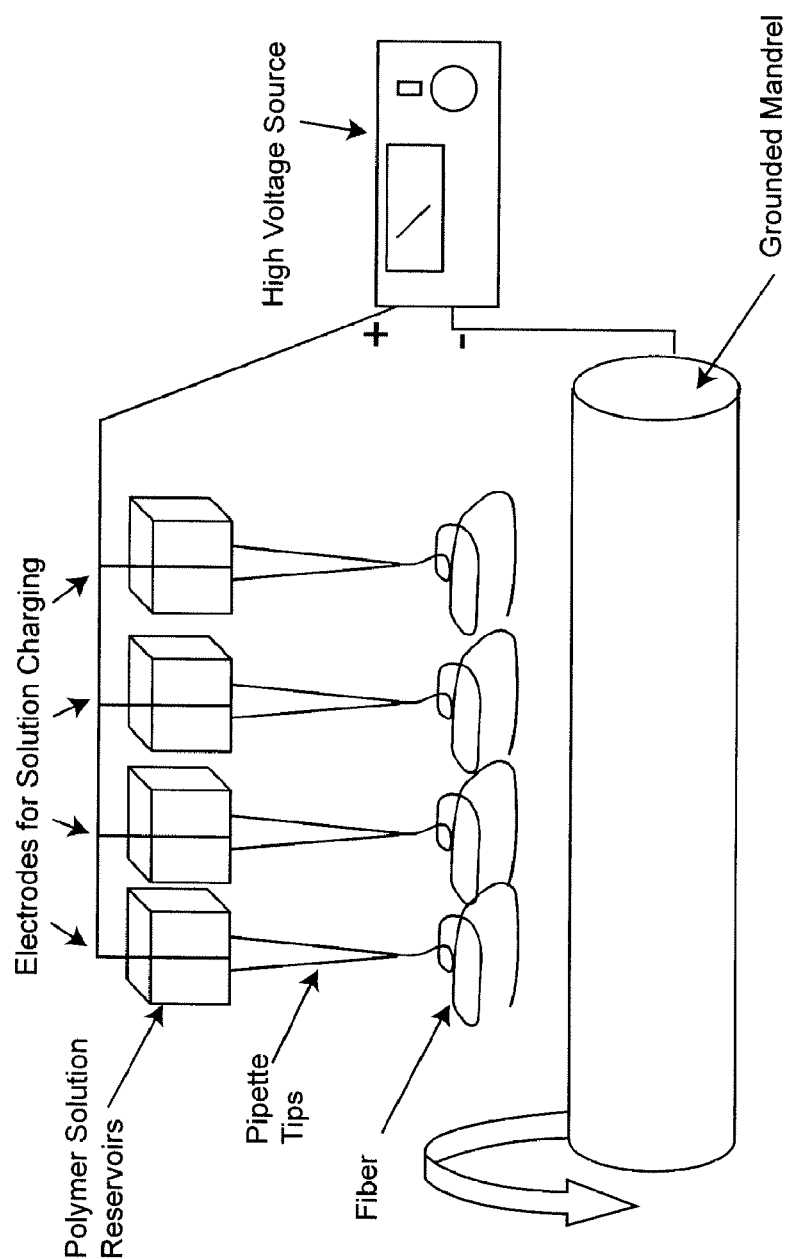

This application is a continuation of U.S. application Ser. No. 12/937,322, filed Feb. 9, 2011, which claims priority to PCT/US09/40182, filed Apr. 10, 2009, which claims priority to U.S. Applic. No. 61/044,165, filed Apr. 11, 2008, the contents of which are incorporated by reference herein.

FIELD OF THE INVENTION

The invention generally relates to dextran fibers, preferably electrospun dextran fibers, and devices formed therefrom. In particular, such devices may be bandages which include therapeutic substances associated with the electrospun fibers, which, upon exposure to a liquid that dissolves the electrospun fibers, are released into the liquid.

BACKGROUND OF THE INVENTION

The body's natural response to stem bleeding from a wound is to initiate blood clotting via a complex process known as the coagulation cascade. The cascade involves two pathways that ultimately lead to the production of the enzyme thrombin, which catalyzes the conversion of fibrinogen to fibrin. Fibrin is then cross-linked to form a clot, resulting in hemostasis. For wounds that are not severe, and in individuals that have no countervening conditions, the body is usually able to carry out this process efficiently in a manner that prevents excessive loss of blood from the wound. However, in the case of severe wounds, or in individuals in whom the clotting mechanism is compromised, this may not be the case. For such individuals, it is however possible to administer components of the coagulation cascade, especially thrombin and fibrinogen, directly to the wound to bring about hemostasis. Bandaging of bleeding wounds is also a usual practice, in part to isolate and protect the wounded area, and also to provide a means to exert pressure on the wound, which can also assist in controlling bleeding.

While these methods may be carried out satisfactorily in cases of mild trauma or under conditions of "controlled" wounding (e.g. surgery), many situations in which such treatments are most needed are also those in which it is the most difficult to provide them. Examples of such wounds include, for example, those inflicted during combat, or unanticipated wounds that occur as the result of accidents. In such circumstances, survival of the wounded individual may depend on stopping blood loss from the wound and achieving hemostasis during the first few minutes after injury. Unfortunately, given the circumstances of such injuries, appropriate medical intervention may not be immediately available.

In particular, the treatment of penetrating wounds such as bullet wounds or some wounds from shrapnel is problematic. This is due to the difficulty in placing a bandage and/or therapeutic agents at the actual site of injury, which includes an area that is well below the body surface and difficult or impossible to access using conventional techniques.

Jiang et al. (Biomacromolecules 2004, 5, 326-333) teaches electrospun dextran fibers. Agents associated with the fibers (e.g. BSA, lysozyme) are directly electrospun into the fibers. The fibers may also include other polymers electrospun with the dextran.

Jiang et al. (2006, Journal of Biomedical Materials Research Part B: Applied Biomaterials, 50-57, Wiley Periodicals, Inc.) discloses electrospun fibers which are a composite of poly(c-caprolactone) as a shell and dextran as a core. These fibers provide the slow release of agents (bovine serum albumin, BSA) which are also electrospun into the fibers.

U.S. Pat. No. 6,753,454 to Smith et al. (Jun. 22, 2004) discloses electrospun fibers comprising a substantially homogeneous mixture of a hydrophilic polymer and a polymer which is at least weakly hydrophobic, which may be used to form a bandage. The bandage may comprise active agents (e.g. dextran). However, the disclosed fibers are not readily soluble in liquid.

U.S. Pat. No. 6,762,336 to MacPhee et al. (Jul. 13, 2004) teaches a hemostatic multilayer bandage that comprises a thrombin layer between two fibrinogen layers. The bandage may contain other resorbable materials such as glycolic acid or lactic acid based polymers or copolymers. Neither electrospun fibers nor dextran fibers are taught as components of the bandage.

U.S. Pat. No. 6,821,479 to Smith et al. (Nov. 23, 2004) teaches a method of preserving a biological material in a dry protective matrix, the matrix comprising fibers such as electrospun fibers. One component of the fibers may be dextran, but homogeneous dextran fibers are not described.

U.S. Pat. No. 7,101,862 to Cochrum et al. (Sep. 5, 2006), teaches hemostatic compositions and methods for controlling bleeding. The compositions comprise a cellulose containing article (e.g gauze) to which a polysaccharide is covalently or ionically crosslinked. The crosslinked polysaccharide may be dextran. However, the compositions are not electrospun and exogenous clotting agents are not included in the compositions.

United States patent application 2004/0018226 (Wnek et al., published Jan. 29, 2004) discloses fibers produced by an electroprocessing technique such as electrospinning. The fibers comprise enclosures within the fibers for containing substances that are not miscible with the fibers. Dextran is not taught as a fiber component.

United States patent application 2007/0160653 (Fisher et al., published Jul. 12, 2007) teaches a hemostatic textile comprising hemostatic factors (e.g. thrombin, fibrinogen) but the fibers are formed from electrospun glass plus a secondary fiber (e.g. silk, ceramic, bamboo, jute, rayon, etc.)

United States patent application 2008/0020015 (Carpenter et al., published Jan. 24, 2008) teaches wound dressing comprised of various biodegradable polymers and hydrogels having allogenic or autologous precursor cells (e.g. stem cells) dispersed within the polymers. The polymers may be prepared by electrospinning, and one polymer component may be dextran. However, the polymers cannot be immediately soluble upon contact with liquid, as they must provide a scaffolding for delivery of the cells over time, even though the polymers eventually biodegrade in situ.

United States patent application 2008/0265469 (Li et al., priority date: Nov. 10, 2006) describes electrospun nanofibers which may comprise dextran. However, the nanofibers are not described as readily soluble in liquids.

United States patent application 2009/0053288 (Eskridge et al., published Feb. 26, 2009) teaches a woven hemostatic fabric comprised of about 65% fiberglass yarn and about 35% bamboo yarn. The fiberglass component may be electrospun, and hemostatic factors such a thrombin may be associated with the fabric, e.g. by soaking the material in a solution of thrombin. Dextran may be added as a hygroscopic agent.

There is an ongoing need to provide improved methods and means to initiate blood clotting in wounds in order to stop or at least slow blood loss. In particular, there is an ongoing need to improve the capability to readily promote hemostasis in severe wounds in a facile manner, especially under circumstances where immediate treatment by medical personnel is limited or unavailable.

SUMMARY OF THE INVENTION

Electrospun dextran fibers (EDFs) are demonstrated herein to be useful as a temporary "scaffolding" to sequester and transport one or more associated substances of interest to a location of interest. A liquid solvent is present at or will be present at the location of interest, and the scaffolding is temporary because the electrospun dextran fibers dissolve upon contact with the liquid, releasing the associated substances of interest into the liquid. In one embodiment of the invention, the EDFs are fabricated into a bandage which also includes therapeutically beneficial active agents, usually bioactive agents. For example, the bandage may include substances that promote hemostasis such as thrombin and fibrinogen. In this embodiment, the thrombin and fibrinogen are present within the bandage in forms that are active upon contact with liquid such as blood. Application of the bandage to a bleeding wound results in dissolution of the dextran fibers in the liquid blood, and release of active thrombin and fibrinogen directly into the wound bed. The active thrombin rapidly catalyzes the conversion of the fibrinogen to fibrin, and formation of a hemostatic plug or clot from fibrin ensues, resulting in hemostasis.

The use of electrospun dextran for the delivery of substances of interest to a liquid environment of interest has many advantages over the prior art. For example, electrospun dextran fibers are extremely light-weight and flexible (malleable), and thus devices made from electrospun dextran fibers have very small footprints. This is important in many situations. For example, bandages made according to the invention are readily accommodated in, e.g., the gear carried by a soldier, without adding excessive weight or bulk. In addition, upon contact with liquid, electrospun dextran dissolves instantaneously (or nearly instantaneously) and completely. Therefore, when placed, for example, on or over a bleeding wound, agents included in the bandage are rapidly and directly delivered to the wound site, and a clot is formed. There is no need to remove the dextran components of the bandage, possibly disrupting the clot, because the dextran component dissolves. Advantageously, implementation of this potentially life-saving technique does not require the use of sophisticated instrumentation or a high level of training or expertise; such devices can be administered by a novice, and may even be self-administered if need be. For example, a wounded soldier may be able to self-administer a dextran bandage in order to staunch the flow of blood from a wound, while waiting for medical personnel to further assist him or her.

In some embodiments, the electrospun dextran fiber device includes a non-soluble or partially or slowly soluble support material to provide additional stability to the "cottony" electrospun fibers. The support material may also be formed from electrospun material, such as compressed electrospun dextran, or other electrospun fibers, or from another type of material altogether. If compressed dextran fibers are used, in general a full size bandage contains 5-10 grams of dextran and is perhaps from about 2.5 to about 4 inches in width and length, and bout 2 inches high (depth), and such a bandage can be compressed to about 0.5 inches in depth to form a support material. Advantages of including a support material are, for example, that the device may be somewhat more robust and able to withstand manipulations (packaging, packing, handling, etc.). In the case where the device is a bandage, the presence of the support material makes it possible to apply pressure through the bandage and onto a wound to which the bandage is applied, even though the dextran fibers and active agents dissolve immediately upon exposure to liquid blood.

It is an object of this invention to provide a method of delivering one or more agents of interest to a location of interest. The method comprises the step of applying or delivering to said location of interest a device, the device comprising 1) electrospun dextran fibers which dissolve upon contact with liquid; and 2) one or more agents of interest associated with the electrospun dextran fibers. The step of applying or delivering results in dissolution of the electrospun dextran fibers in liquid at the location of interest, thereby releasing the one or more agents of interest into the liquid. In some embodiments, the electrospun dextran fibers have a diameter ranging from 0.75 microns to 1.00 micron. In some embodiments, the location of interest is a site on a body of a subject; and the liquid at the site may be a bodily fluid. In addition, the one or more agents of interest may be bioactive agents.

The invention further provides a bandage comprising electrospun dextran fibers which have a diameter ranging from 0.75 microns to 1.25 microns, and which dissolve upon contact with liquid; and at least one of thrombin and fibrinogen are associated with the electrospun dextran fibers in the bandage. In one embodiment of the invention, the thrombin and fibrinogen are salmon thrombin and salmon fibrinogen, which may be in particulate form. Alternatively, the thrombin and fibrinogen may be present within electrospun droplets. In some embodiments of the invention, both thrombin and fibrinogen are associated with the electrospun dextran fibers. In other embodiments, the bandage further comprises one or more additional bioactive agents. In yet other embodiments, the bandage comprises a support material. In some embodiments, the support material comprises a material selected from gauze, compressed electrospun dextran, polyglycolytic acid polymers, polylactic acid polymers, caprolactone polymers and charged nylon.

The invention also provides a method of inducing hemostasis in a wound. This method comprises the step of applying to the wound a hemostatic bandage which comprises: 1) electrospun dextran fibers which have a diameter ranging from 0.75 microns to 1.25 microns, and which dissolve upon contact with liquid; and 2) at least one of thrombin and fibrinogen associated with the electrospun dextran fibers. The step of applying results in dissolution of the electrospun dextran fibers in blood within the wound and release of the thrombin and fibrinogen into the blood within said wound, thereby inducing hemostasis in the wound. In some embodiments, both thrombin and fibrinogen are associated with the electrospun dextran fibers.

BRIEF DESCRIPTION OF THE DRAWINGS

FIG. 1. Schematic of the electrospinning apparatus. The key elements of the electrospinning system include a high voltage power supply, a source reservoir for the polymer and a grounded mandrel. This system utilizes a cylindrical target mandrel; however the electrospinning process can be adapted to produce much more complex shapes. Single and/or multiple polymers can be independently or simultaneously delivered to the electric field from one or more source reservoirs. Electrospinning distinct and unique polymers from separate sources in a temporal sequence can be used to produce a laminated structure.

Figure 2A:
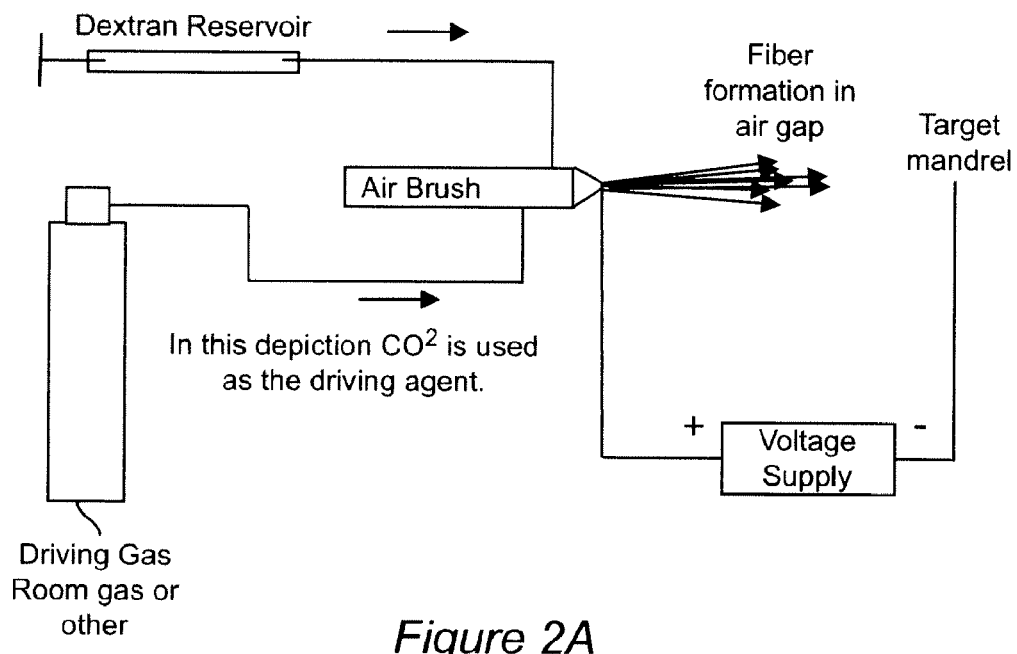
Figure 2B:
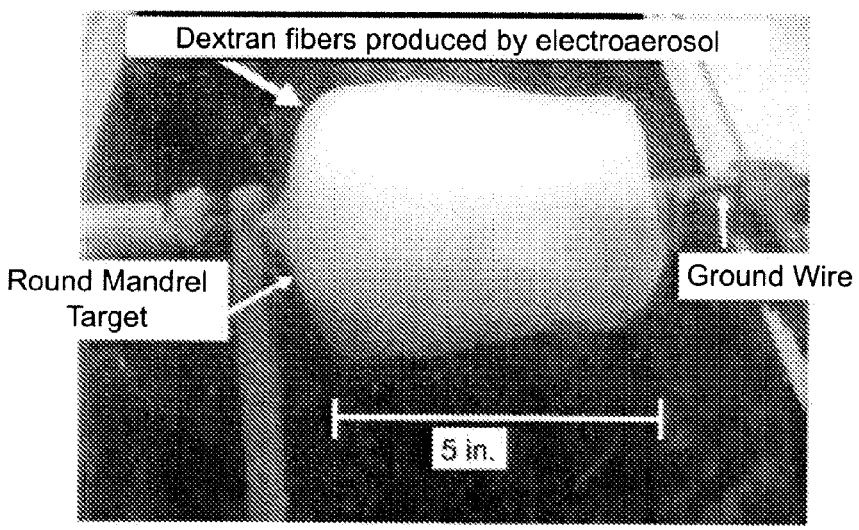

FIGS. 2 A and B. A, schematic of air brush based dextran processing; B, dextran fibers produced by electroaerosol processing. The amount of material depicted is probably enough material for about two bandages. Note the loft of the material. An electric field was used to target the dextran to the mandrel.

Figure 3:
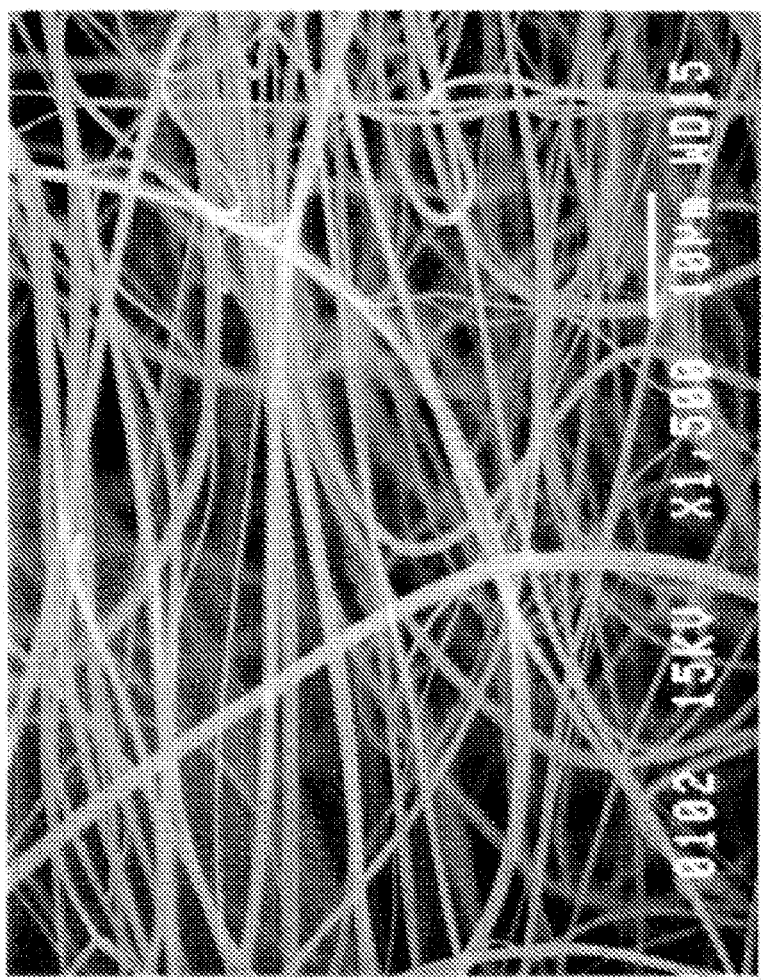

FIG. 3. Scanning electron micrograph of electrospun dextran fibers. The nominal average cross sectional diameter of the individual fibers was 1 micron, providing a large surface area.

FIG. 4A-E. Schematic representations of exemplary bandages formed form electrospun dextran fibers. A, bandage with non-permeable support material as a backing; B, bandage with net-like support material; C, bandage with non-permeable backing and a net-like support material holding the electrospun fibers in place on the backing; D, bandage (device) for delivery of therapeutics to a deep wound; E, alternative embodiment of a device for delivery of therapeutics to a deep wound.

Figure 5A:
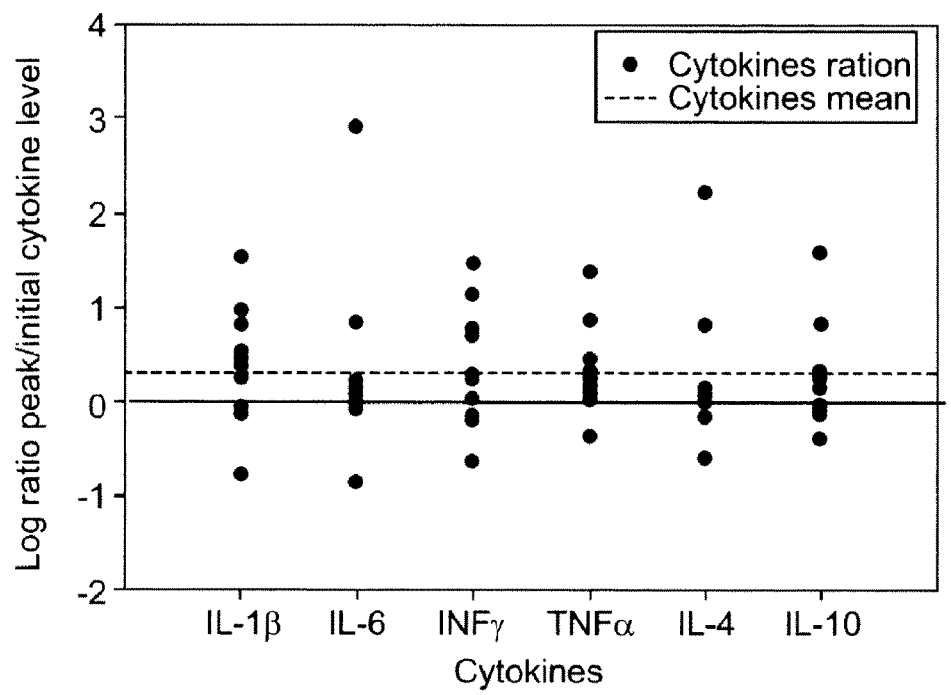

FIGS. 5A and B. Changes in cytokine levels in animals exposed to the salmon fibrinogen/thrombin bandage. (A) Levels of IL-1$\beta$, IL-6, TNF-$\alpha$, IFN-$\gamma$, IL-4 and IL-10 are shown as the log ratio of the cytokine level determined in blood drawn at the initial surgery to implant the vascular port compared to peak levels following exposure. Changes were seen in both pro-inflammatory responses (IL-1$\beta$, IL-6, TNF-$\alpha$, IFN-$\gamma$) and humoral responses (IL-4 and IL-10). (B) Changes in the cytokines within an individual animal show that initial exposure (first arrow) and the subsequent intravenous infusion of proteins (second arrow) elicited a response that could be detected in samples taken at the next blood draw.

FIG. 6A-F. Qualitative assessment of immunoglobulin production by swine in response to salmon proteins by Western blotting. (A) PAGE of salmon (Sal), human (Hu) and swine (Sw) fibrinogen preparations and corresponding Western blots with serum from two animals (B and C). Serum from pre-exposure and final euthanasia blood draws are presented in these panels. IgG isotypes present in the serum were visualized by specific HRP anti-swine IgG second antibodies and are detected as binding to the proteins in the gel samples. Arrows indicate the positions of the IgG heavy and light chains components in the swine protein lanes which are also recognized by the 2nd antibody. Molecular weights are show to the left (kDal×10–3). (D) PAGE of salmon (Sal), human (Hu) and swine (Sw) thrombin preparations and corresponding Western blots with serum from the same animals shown in (C and D). In these animals, thrombin was not recognized in E, but there is a faint reaction in the salmon protein lane in F (arrow). The camera in the detection system detected the heavy swine thrombin protein on the membrane as a white band in F.

FIG. 7A-D. Time course of antibody development in animals exposed to salmon thrombin/fibrinogen bandages through the dermal patch protocol. ELISAs were performed using anti-IgG reagents. The following antigens were used as the targets in the ELISAs: (A) salmon fibrinogen, (B) salmon thrombin, (C) human fibrinogen and (D) human thrombin. The increases in absorbance observed at the later samples panels A, B, C occurred following intravenous infusion of salmon proteins. Each curve represents data from a different animal.

FIG. 8A-D. Time course of antibody development in animals exposed to salmon thrombin/fibrinogen bandages through the abdominal patch protocol. ELISAs were performed using anti-IgG reagents. The following antigens were used as the targets in the ELISAs: (A) salmon fibrinogen, (B) salmon thrombin, (C) human fibrinogen and (D) human thrombin.

FIG. 9A-D. Progression of dermal healing following full-thickness wound. Images from samples taken at 7 days from control (A) and salmon bandage-treated (B) injuries show a fibrinonecrotic coagulum filling the wound defect (*) and an epithelial cell projection towards wound center in both cases as wound healing progresses following initial clotting. (H&E staining, bars=100 um). Samples taken at 28 days from control (C) and salmon bandage-treated (D) injuries show complete re-epithelialization by a hyperplastic and hyperkeratotic epidermis. (H & E staining, bars=100 um).

Figure 10:
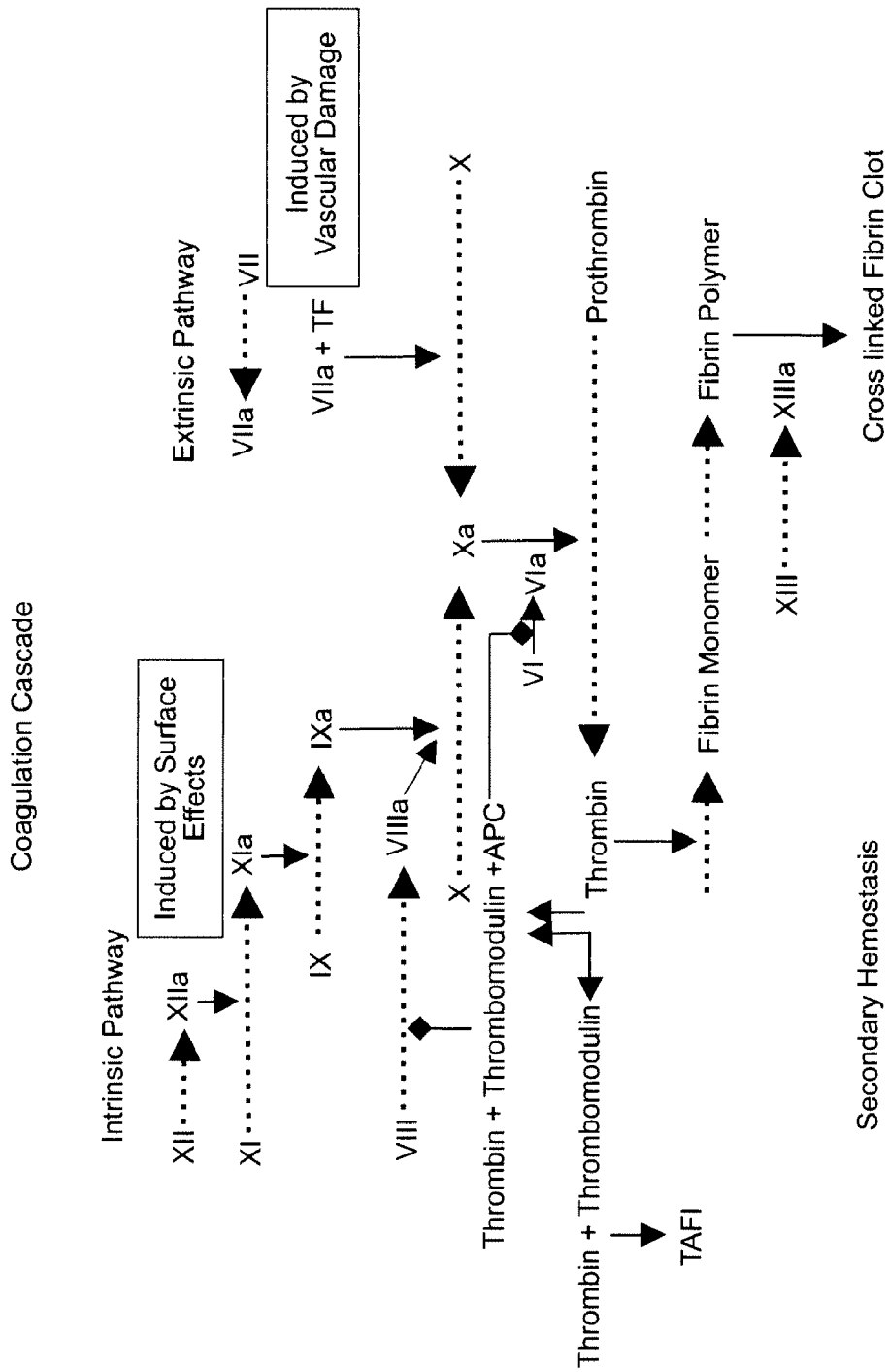

FIG. 10. Schematic of the coagulation cascade.

DETAILED DESCRIPTION OF THE INVENTION

The invention provides dextran fibers, especially electrospun dextran fibers. The electrospun dextran fibers (EDFs) may be formed into a variety of devices for a variety of purposes. Generally, one or more substances of interest are associated with the EDFs in the device, usually for the purpose of delivering the one or more substances of interest to a liquid of interest. Upon contact with the liquid, the EDFs dissolve almost immediately and the associated substances are released into the liquid milieu.

In one embodiment of the invention, the EDFs are formed into a bandage. The bandage generally includes active agents associated with the EDFs, the active agents being delivered to a site of action (e.g. a wound) via application of the bandage to the site. The site of action contains or will contain a liquid, and when the bandage is applied to the site of action, the EDFs of the bandage dissolve in the liquid, and the active agents associated with or sequestered in or around the mat of dextran fibers are released into the liquid. In one embodiment, the site of action is a wound bed, and the active agents that are delivered by the bandage are factors or agents that participate in the coagulation cascade such as thrombin and fibrinogen. Application of an EDF bandage to a wound results in dissolution of the dextran fibers in blood within the wound bed, which in turn results in release or delivery of the active agents at or into the site. Thrombin and fibrinogen that are associated with the bandage are in forms that are biologically active when they come into contact with blood. Hence, upon dissolution, the thrombin acts on the fibrinogen, converting it to fibrin, which then forms a clot within the wound, staunching the flow of blood. In some embodiments of the invention, only spun dextran fibers are utilized and thus after clot formation, there is no need to disturb the clot in order to remove bandage components, since none remain at the site. In other embodiments, as described below, the bandage may comprise other materials such as support or backing material, which, after initial rapid application of the bandage, may later be removed for further treatment of the wound by conventional methods.

Electrospinning is a non-mechanical processing strategy and can be scaled to accommodate the large volumes necessary to meet the needs of commercial processing. A schematic representation of one type of set-up for electrospinning is provided in FIG. 1. In this process a polymer solution, or melt, is injected with current to create a charge imbalance. The charged solution is then placed in proximity to a grounded target (in FIG. 1, a grounded mandrel). At a critical voltage the charge imbalance begins to overcome the surface tension of the polymer source, forming an electrically charged jet. Within the electric field, the jet is directed towards the grounded target and the carrier solvent evaporates. Depending upon reaction conditions, and the polymers used in the process, electrospinning can be utilized to produce a fine aerosol of material or a continuous non-woven mat of fibrillar material, as shown in FIG. 1. For many polymers, the nature of the electrospinning process intrinsically provides a high degree of control over the diameter of the resulting fibers. Micron to nanoscale diameters can be selectively achieved simply by regulating the starting concentrations of the polymers present in the electrospinning solutions. By controlling the motion of the ground target with respect to the source solution, fibrils may be deposited into a random matrix or into aligned arrays that are oriented along a defined axis.

A second schematic of an electrospinning apparatus is shown in FIG. 2A. The key elements of the electrospinning system include a high voltage power supply, a source reservoir for the polymer and a grounded target mandrel. The system that is depicted utilizes a cylindrical target mandrel; however the electrospinning process can be adapted to produce much more complex shapes. Single and/or multiple polymers can be independently or simultaneously delivered to the electric field from one or more source reservoirs. In addition, electrospinning distinct and unique polymers from separate sources in a temporal sequence can be used to produce a laminated structure. FIG. 2B shows the result of electrospinning about 10 g of dextran dissolved in deionized water onto a round mandrel target, as described in detail in the Example 1 below. FIG. 3 shows a scanning electron micrograph of electrospun dextran fibers in which the average cross sectional diameter of the individual fibers is about 1 micron.

Those of skill in the art will recognize that electrospinning is not the only way to make dextran fibers. Such fibers may be produced by other methods of aerosolization. However, the electric field helps in the efficient collection of the fibers, and electrospinning may yield more uniform fibers. Other technologies which might also be employed for spinning dextran fibers, including those described in U.S. Pat. No. 7,067,444 to Luo et al. (Jun. 27, 2006); U.S. Pat. No. 6,116,880 to Bogue et al. (Sep. 12, 2000); and U.S. Pat. No. 5,447,423 to Fuisz et al. (Sep. 5, 1995), the complete contents of each of which are hereby incorporated by reference. In particular, so-called "cotton-candy machines" (with or without applied electrostatic force) may be suitable for use in fabricating the dextran fibers of the invention. More detailed descriptions of methods of preparing the dextran fibers of the invention are provided in Example 2 below. Other methods include compressing a dextran solution between two plates or other flat surfaces and drawing the plates or surfaces away from each other, usually repeatedly. Dextran fibers form between the two surfaces.

In some embodiments, substances other than dextran are used to form fibers for use in the devices of the invention, especially (but not exclusively) when a cotton-candy machine is employed. Examples of such substances include but are not limited to sugars such as dextrose, sucrose, etc.

The commercially available dextran that is used to produce the electrospun fibers of the invention is synthesized from sucrose by enzymes on the cell surface of certain lactic acid bacteria, the best-known being *Leuconostoc mesenteroides* and *Streptococcus mutans*. Dextran is a complex, branched glucan (a polysaccharide made of many d-glucose molecules) composed of chains of varying lengths (e.g. from 10 to 200 kilodaltons). The straight chain consists of α-1,6 glycosidic linkages between glucose molecules, while branches begin from α-1,4 linkages (and in some cases, α-1,2 and α-1,3 linkages as well). Dextrans are commercially available in a wide range of molecular weights e.g. from about 10 kilodaltons (kDa) to about 200 kDa. Commercial preparations are mixtures of dextrans of varying molecular weights, usually in narrower weight ranges and may be provided, for example, as "low" or "high" molecular weight dextrans. For example, "Dextran 40" has an average molecular weight of 40 kDa, "Dextrans 75" has an average molecular weight of 75 kDa, etc. In the practice of the present invention, the dextrans used for electrospinning are typically in a molecular weight range of from about 10 to about 200 kDa, or from about 25 to about 200 kDa, or from about 50 to about 200 kDa, or from about 75 to 200 kDa, and usually from about 60 to 90 kDa, or from about 100 to about 200 kDa. Further, as would be understood by those of skill in the art, the median size of the dextran molecules in a dextran preparation also has an effect in that if the median weight is high in a particular lot, less dextran may be used to form the desired amount of fibers.

In general, the conditions for electrospinning dextran are as follows: an ambient temperature of from about 60 to about 75° F.; a relative humidity of from about 30% to about 40%, and typically at least about 20%. The resulting fibers are typically in the nanometer or mm range of cross-sectional diameter, usually from about 0.75 microns to about 1.25 microns. The electrospun fibers are "dry" and should be protected from exposure to moisture to prevent premature dissolution. However, some water is associated with the fibers and fiber compositions can contain from about 7 to about 8% water, but must be less than about 5% when the fibers are sterilized by x-ray irradiation.

The devices of the invention are usually formed of substantially homogeneous spun dextran. The amount of dextran per device can vary widely, depending on the size of device that is being manufactured, with typical device formulations using from about 5-10 g of dextran (usually 100,000-200,000 Mr) per device. However, the range can be extended widely, e.g. from as low as about 0.5 g or less (for small devices) to as high as 100 or more g per device, for large devices. In some embodiments of the invention, is may be helpful to use lesser amounts of dextran (e.g. about 0.1 to about 0.5 g of dextran per device) in order to concentrate the active agents that are delivered by the device into a smaller volume. Of more consequence is the concentration of dextran in the solution from which the fibers are spun. Generally, a solution of dextran for electrospinning will be of a concentration in the range of from about 0.1 to about 10 grams per ml of solvent, or from about 0.5 to about 5 grams per ml, and usually such a solution is at a concentration of about 1 gram per ml, ±about 0.15 mg. A preferred range would be from about 0.9 to about 1.1 grams of dextran per ml of solution that is to be spun. Those of skill in the art will recognize that, due to the variability of molecular weight ranges in dextran preparations, and due to inherent variability from batch to batch of commercially available preparations purporting to be of a particular molecular weight range, it is typically necessary to test each batch of dextran with respect to electrospinning properties. Such tests are well within the purview of one of skill in the art, and usually involve trials of electrospinning a range of concentrations of dextran dissolved in a suitable solvent, in order to ascertain which concentration(s) result(s) in the most desirable fiber characteristics, e.g. stability (e.g. to heat, humidity, etc.), uniformity, cross-sectional diameter, etc. Those of skill in the art will recognize that critical indicators of success are very obvious when trying a new batch of dextran. Too little dextran in the spinning solution results in "spitting" from the needle, whereas too much dextran results in the production of dried droplets, or failure to spin at all. Likewise, when the humidity is too low, similar results can occur, i.e. fibers fail to form and in some cases fail to target efficiently to the ground. These characteristics can be assessed according to methods that are well known to those of skill in the art, including but not limited to visual observation, testing of fiber strength and flexibility, observation via electron microscopy, solubility testing, resistance to heat and/or irradiation, color and tendency to discoloration, etc. As would be understood by those of skill in the art, all such testing may be carried out under varying conditions of heat, humidity, etc. Formulations may also be assessed using animal testing.

The area (length and width) of a device of the invention can vary widely and can be adjusted by adjusting spinning parameters. In addition, the mats of dextran fibers can be cut to a desired size after spinning. Generally, a device will be from about 0.5 cms or less to about 30 cms or more in length and/or width, but larger or smaller sizes are also contemplated. The height or thickness of a device can likewise vary considerably, e.g. from 0.5 cm or less (e.g. about 0.1, 0.2, 0.3, or 0.4 cm) up to any desired thickness, e.g. from about 1 to about 30 cm, or usually less, e.g. from about 1 to about 20 cm, or from about 1 to about 10 cm, or even from about 1 to about 5 cm, e.g. devices with a thickness of about 1, 2, 3, 4, 5, 6, 7, 8, 9, or 10 cm are usual. The thickness of the device (which is related to the volume) may impact the rate of dissolution of the dextran upon contact with liquid. For example, a thin device (e.g. about 2 cm or less, or about 1 cm or less, or even about 0.5 cm or less, e.g. about 0.4, 0.3, 0.2, or 0.1 cm), e.g. a thin sheet, will dissolve more rapidly than a device that is thicker, providing the loft of the fibers is comparable. In most embodiments, dissolution of the dextran fibers is extremely rapid, e.g. about 5 minutes or less after exposure to liquid, or about 4 minutes or less, or about 3 minutes or less, or about 2 minutes or less, or about 1 minute or less, e.g. the device typically takes only a few seconds to dissolve (e.g. from about 1 to about 60 seconds, or from about 1 to about 45 seconds, or from about 1 to about 30 seconds, or from about 1 to about 20, 15, 10, or 5 seconds or less to dissolve. This rapid dissolution may be referred to herein as "instantaneous" or "immediate" dissolution. Compression of an electrospun dextran mat may be used to modulate the rate of dissolution, with greater levels of compression inversely impacting the rate, i.e. generally, the greater the degree of compression, the slower the rate of dissolution. The rapid rate of dissolution is advantageous, particularly when delivering biologically active agents (e.g. hemostatic agents) to a site of action such as a wound. Rapid dissolution of the carrier dextran fibers provides extremely rapid delivery of the hemostatic agents to the wound upon deployment of the device.

Those of skill in the art will recognize that a plethora of liquid solvents exist in which it is possible to dissolve dextran. However, superior results for electrospinning dextran are generally achieved when the solvent is water, especially deionized or distilled or deionized, distilled (ddH2O) or other forms of relatively pure water. In addition, there is far less environmental impact associated with the use of water. It has been found that, generally, high concentrations of salt in the solvent should be avoided. Whereas salt is often used to facilitate the spinning of some electrospun polymers, this is not the case for dextran. The concentration of salts in the spinning solution should be kept at a minimum to successfully form dextran fibers.

The one or more active agents that are associated with the dextran fibers of the bandage may be any active agent that it is desirable or advantageous to deliver to the site where the EDF device is to be used or applied. In one embodiment of the invention, the EDF device is a bandage and is used to deliver beneficial agents, for example, to a wound. Such wounds include wounds and breaches of body or tissue integrity that occur as a result of trauma (e.g. accidental trauma, trauma resulting from conflicts such as gunshot wounds, knives, etc.), as well as wounds which are purposefully incurred, such as surgical incisions, body piercings, etc. Usually the agents are bioactive agents that have a beneficial or therapeutic effect at the wound site. In one embodiment, the site is a bleeding wound at which it is desired to form a blood clot in order to stop or slow the bleeding. In this embodiment, the therapeutic substances of interest may include, for example, thrombin and fibrinogen, although other agents active in promoting hemostasis, including but not limited to capscian, may also be included. In addition, electrospun or non-electrospun collagen, agents that absorb water, various dry salts that would tend to absorb fluids when placed in contact with e.g. blood; engineered thrombin or thrombin mimics; engineered fibrinogen; agents that cause vasospasm (e.g. ADP, 5-hydroxytryptamine, 5-HT and thromboxane, (TXA-2) to help contract and seal a bleeding vessel, etc. may also be included. In addition, other components of the clotting cascade may be added to the bandage, for example: tissue factors that are normally only expressed on the surface of damaged cells and which start the normal clotting cascade; serotonin which enhances platelet clumping and promotes vessel constriction; and other agents that are used to replace missing components of the clotting cascade in hemophilia, for example, factor 7 (which activates the so called external extrinsic coagulation cascade) and crude extracts of platelets. These agents essentially work to "jump start" clotting by initiating the cascade further down the reaction network, as illustrated in FIG. 10. In FIG. 10, the various factors (and their alternative nomenclature and/or characteristics and/or activities) are as follows:

Factor XII (Hageman factor): serine protease, plasma protein binds collagen;

Factor XI (Plasma thromboplastin antecedent): serine protease, plasma protein;

Factor IX (Christmas-Eve Factor): serine protease;

Factor VIII: Glycoprotein binds vWF, produced by endothelium and liver;

Factor VII (Proconvertin): serine protease, Vitamin K dependent synthesis in the liver;

Factor X (Stuart-Prowler Factor, Clotting Factor X): serine endopeptidase, converts prothrombin to thrombin; and Factor XIII (Fibrin stabilizing Enzyme): stabilizes fibrin polymer, plasma protein, also present in platelets and monocyte linage.

In FIG. 10, italic pathways denote inhibition and the central role of thrombin in the activation of coagulation and inactivation of coagulation processes is shown, where:

VI=Cofactor for Xa in the conversion of prothrombin to thrombin;

APC=Activated Protein C, an extracellular signal molecule, inhibits FVI (equivalent to FVa, a cofactor of XA in the conversion of prothrombin to thrombin) and FVIIIa through a proteolytic event; and TAFI=Thrombin Activatable Fibrinolysis Inhibitor, an inhibitor of clot lysis.

In addition, agents which function to promote late stages of wound healing may also be included to, for example, facilitate cell migration and remodeling. The incorporation of collagen is an example of such an agent.

One or more of any of these agents may be used in the practice of the present invention. The therapeutic agents must be amenable to drying and are associated with the electrospun dextran fibers in the dry state, since liquid would dissolve the fibers. For example, the agents may be desiccated or lyophilized, or water may be removed by some other means. Generally, the amount of water that is present in the substances when they are associated with the EDFs is less than about 5%, and preferably less that about 2%. These substances retain full or partial activity when rehydrated, e.g. in blood. Generally therapeutic substances associated with the devices of the invention retain, upon contact with liquid, at least about 25%, or about 50%, or even about 75 to 100% of their activity before drying or desiccation, as compared to standard preparations of the substance using standard assays that are known to those of skill in the art.

In some embodiments, thrombin or fibrinogen, or both, are associated with the bandage. In some embodiments, the thrombin and fibrinogen are salmon thrombin and fibrinogen. Advantages of using salmon as a source of these materials include but are not limited to the lack of concern about transmission of etiologic agents (e.g. viruses) that may occur when human and other mammalian sources of thrombin or fibrinogen (e.g. bovine) are used. As demonstrated in the Examples section below, salmon thrombin and fibrinogen are highly efficacious and have no deleterious side effects, when used in the pig model, which is a recognized animal model that is considered to be indicative of results in humans. The quantity of particulate fibrinogen added to the bandage is generally in the range of from about 1 to about 3 grams per bandage, and usually from about 1.5 to about 2 grams per bandage. For thrombin, the quantity may be from about 100-10,000 units per bandage, and is typically from about 4000-6000 units per bandage.

In some embodiments, the therapeutic agents may themselves be electrospun, either with the dextran (i.e. they are dissolved in and spun from the same solution as the dextran) or separately (they are dissolved in and spun from a separate solution that does not include dextran). In some embodiments, the agents may be electrospun into fibers, as is the case for dextran. In other embodiments, the active agents may be electrospun into other forms such as droplets, beads, etc. In some applications, active agents such as thrombin may be electrosprayed with sucrose to form sugar droplets, which tends to stabilize thrombin and can also "trap" other substances of interest for delivery to the bandage.

In particular, for thrombin and fibrinogen, in most embodiments, these (or other) agents are associated with or added to electrospun dextran fibers in a finely dispersed dry, particulate or granular form e.g. as a fine powder or dust, as electrospinning may tend to decrease their activity. In other words, the agents are not electrospun either by themselves or with the dextran. The provision of the substances in the form of a fine powder provides a large surface area of contact for dissolution when the materials come into contact with fluid. Generally, such particles will have average diameters in the range of from about 1 to about 10,000 microns, and usually from about 10 to about 1000 microns. Such dry solid particles may be formed by any of several means, including but not limited to grinding, pulverizing, crushing, etc. However, those of skill in the art will recognize that other forms of these agents may also be included in the bandage, e.g. flakes, films, sheets, strings, etc. Further, in some embodiments, thrombin and fibrinogen are in the form of electrospun droplets when associated with the EDFs.

Association of substances of interest with the EDFs may be accomplished by any of many suitable techniques that are known to those of skill in the art, and will depend in part on the precise form of the substance and the means at hand. For example, for powdered, particulate thrombin and fibrinogen, association may be carried out by sprinkling, shaking, blowing, etc. the agents onto a layer of EDFs. Depending on the density of the fiber mat, the substances of interest may become relatively evenly dispersed throughout the woven mat of fibers or may be largely confined to the topmost section of the fiber mat. If no backing is present, the latter embodiment is preferable, to prevent the particulate substance of interest from falling through and out of the mat. The density of the fibrous mat can be adjusted (e.g. increased), for example, by adjusting its thickness and/or by compressing the mat under pressure so that the fibers are closer together. Other techniques for association also exist, e.g. the placement of dry but liquid soluble sheets or strips of material onto or between layers of electrospun dextran, electrospinning the added materials as a discrete layer or in discrete layers, etc., and any such technique may be employed. The techniques for assembling the devices of the invention may be carried out manually or may be mechanized, or a combination of manual manipulation and mechanization may be used. For thrombin in particular, 5000 units of thrombin is a very small volume of powder. Therefore, inert carriers or bulking agents such as dextrose may be added to insure more complete dispersal of active agents in the bandage.

The association of substances of interest with the EDFs may be carried out according to many different arrangements. For example, a first layer of EDFs may be formed, and one or more of the substances may be associated with the first layer. Then another second layer of EDFs may be formed on top of the substance(s) of interest, and the same or other substances of interest may be associated with the second layer, and so on. A final or outermost layer of EDFs may be added to prevent the dislodgement of substances of interest from the layer(s) below. The number of layers of EDFs that are used in a device of the invention may vary widely, from as few as 1-2 to as many as several dozen, or even several hundred, depending on the desired characteristics of the device. Typically, a device will contain from about 1-2 and up to about 5-10 layers. The very slight amount of moisture that is present in a prepared bandage may help to trap and retain particles of material on the surface of the bandage.

In some embodiments of the invention, the EDF devices also include one or more support structures or support materials incorporated therein. For example, a backing may be incorporated into the device. The support material may be formed from various electrospun materials such as polyglycolic acid (PGA), polylactic acid (PLA), and their copolymers (PLGAs); charged nylon, etc. In one embodiment, the support material is compressed electrospun dextran fibers. By "compressed EDFs" we mean that EDFs are compressed together under pressure. Compression of EDFs is carried out, for example, under pressure between two plates (e.g. a vice), and can compress a mat of fibers with a height (thickness) of about 3 inches to a sheet with a height of about 0.5 inches or even less (e.g. about 0.1 to about 0.4 inches). In some embodiments, the EDFs are electrospun directly onto a previously electrospun support material, while in other embodiments, the support material and the EDFs are associated after electrospinning of each, e.g. by joining of one or more layers of each.

In other embodiments, the support material is not an electrospun material but is some other (usually lightweight) material on which EDFs can be formed, or associated with after electrospinning Examples of such materials include but are not limited to gauze; various plastics; hydrogels and other absorbent materials that can facilitate absorption of blood and therefore clot formation; etc.

The support material may or may not be soluble in liquid, or may be slowly soluble in liquid, and may or may not be permeable to liquid. Slowly soluble materials include those from which absorbable or dissolving (biodegradable) stitches or sutures are formed, included PGA, polylactic and caprolactone polymers. Such support materials typically dissolve within from about 10 days to 8 weeks, depending on the material that is used, and provide the advantage of, in some cases, not having to remove the bandage and risk disrupting the clot. However, in any case, the support material should not interfere with the immediate dissolution of the EDFs and delivery of the active agents associated therewith into the liquid that dissolves the EDFs. Thus, the support material might be only on one side of the EDF device, so that when the device is, for example, a bandage, and is applied to a wound, the bandage is oriented so that the EDFs come into direct contact with the blood in the wound bed and the support material does not, i.e. the support material is the "top" or outermost surface of the bandage when placed on the wound. This embodiment is illustrated, for example, in FIG. 4A, in which EDFs 10 are shown as deposited onto non-porous, liquid impermeable support material 20. When applied to a wound, EDFs 10 would face downward into the wound, and non-porous support material 20 would face away from the wound. This arrangement could provide an advantage in that pressure could be applied to the wound through the support material, to facilitate the stoppage of bleeding. Alternatively, the support material may contain pores, openings or spaces that allow liquid to access the EDFs of the device even when the support material is present. For example, the support material may be a net or web of material that is insoluble (or slowly soluble) but that permits liquid to freely access the EDFs and associated substances of interest. This embodiment is illustrated schematically in FIG. 4B, which shows EDFs 10 deposited on (or possibly under, or on and under, or woven throughout) netting 40, which is shown partially in phantom where covered by EDFs 10. In yet other embodiments, both a "backing" or "top" support material and a second web-like support material may be present in the devise. This embodiment is illustrated schematically in FIG. 4C, which shows EDFs 10 deposited on non-porous support material 50 and overlaid with net-like material 60, i.e. EDFs 10 are "sandwiched" between non-porous support material 50 and net-like material 60.

One of skill in the art will be able to envision many other combinations and shapes of EDF layers and support materials that would provide advantages in particular scenarios. For example, EDFs might be wrapped or wound around an elongated support such as a filament or string, or wrapped around a particular form with the shape of a cavity in which the device is likely to be placed, such as a bullet hole, etc. The crux of the problem at the site of a penetrating injury is that the wounded tissue is relatively inaccessible. For example, for a bullet wound (e.g. in the leg or thigh) bleeding does not occur as much at the surface but deeper within the tissue, within a cavity formed by the bullet, where it can not be easily treated by a bandage that is simply spread over the external site of the injury (e.g. the point of entry of the bullet, knife, shrapnel, sword, bayonet, etc., or other cause of injury). This aspect of the invention solves the problems associated with penetrating injuries, which can cause extensive bleeding in the deep tissues, and takes advantage of the highly soluble nature of the dextran bandage. A complicating factor in this type of injury concerns the ability to deliver hemostatic materials that are highly soluble to such a site. There may be bleeding and other fluids evident at the entry site of the wound and the application of a bandage to this superficial site may result in the complete dissolution of the bandage at the surface-without the delivery of the active materials to the underlying source of the bleeding within the wound cavity. The invention circumvents this occurrence by providing delivery of active agents deep into the wound. Prior art bandages have failed to adequately address this problem.

The present invention solves this problem by providing a device, the shape and application of which can be adapted to use with such wounds. For example, an elongated cylindrical "cigar-shaped" device comprised of spun dextran as described herein, and which also contains particulate thrombin or fibrinogen or both, and which may contain support material, is provided. The device is stored within a protective covering or packaging or tube. This tube protects the bandage (device) from the ambient environment. Both the bandage and the tube are preferably sterile, and may be, for example, optionally further enclosed in an outer wrapper of e.g. paper, polymer, blister pack, similar to that used for disposable syringes, to prevent loss of sterility. When used, the outer wrapping is torn open and the sterile tube containing the bandage is accessed. In some embodiments, one end of the tube is removed and placed over the outermost accessible portion of the injury. The tube may also comprise a "plunger" or similar means which enables the user to expel the bandage from the tube and into the wound, in effect "injecting" the bandage into the wound. Means such as those that are used for the vaginal delivery of, for example, tampons, (i.e. a "cylinder within a cylinder") may be employed, or a syringe-like means of delivery may be used. The device can thus be introduced deep into the tissue along the wound track and the therapeutic agents in the device are delivered to where they are most needed, i.e. to the interior of the wound. In other embodiments, a plunger per se is not included, but the tube is fashioned so that both ends can be opened, and the spun dextran device can be pushed into the wound from one open end by exerting pressure on the opposite open end of the tube using any object that fits at least partially into the tube, sufficiently to push the device out of the tube and into the wound, e.g. a finger, stick, etc. Such an object may be included with the device of the invention. Those of skill in the art will recognize that, due to the relatively high malleability of spun dextran, this embodiment of the device may include support material around or within the spun dextran (e.g. biologically compatible netting, rod, etc. that will disintegrate via biodegradation) in order to render the device more robust and less flexible as it is shunted down into the wound. Further, the outermost end of the device, that end on which pressure is exerted (e.g. with a plunger) in order to expel the device from the tube into the wound, may be reinforced with support material so that the plunger or other object used to push on the device can deliver sufficient force to remove the device from the tube.

Figure 4A:
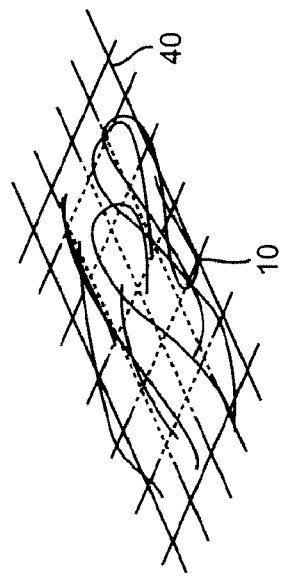
Figure 4B:
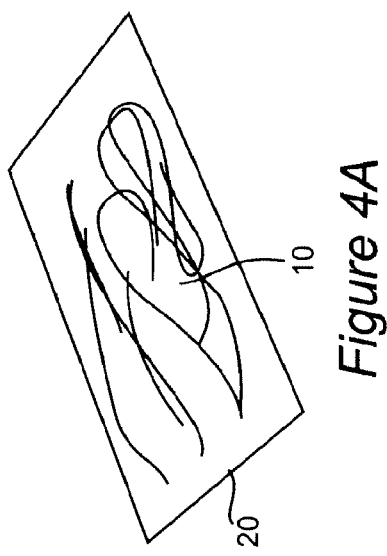
Figure 4C:
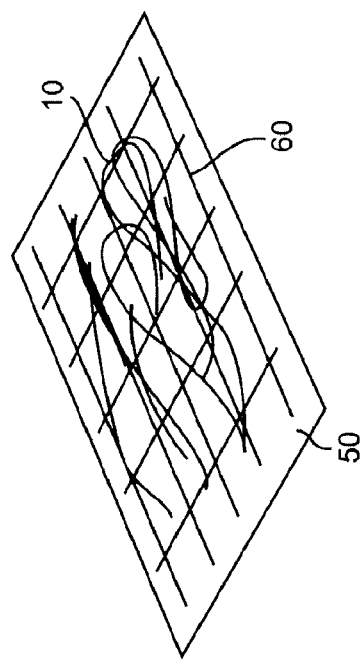
Figure 4D:
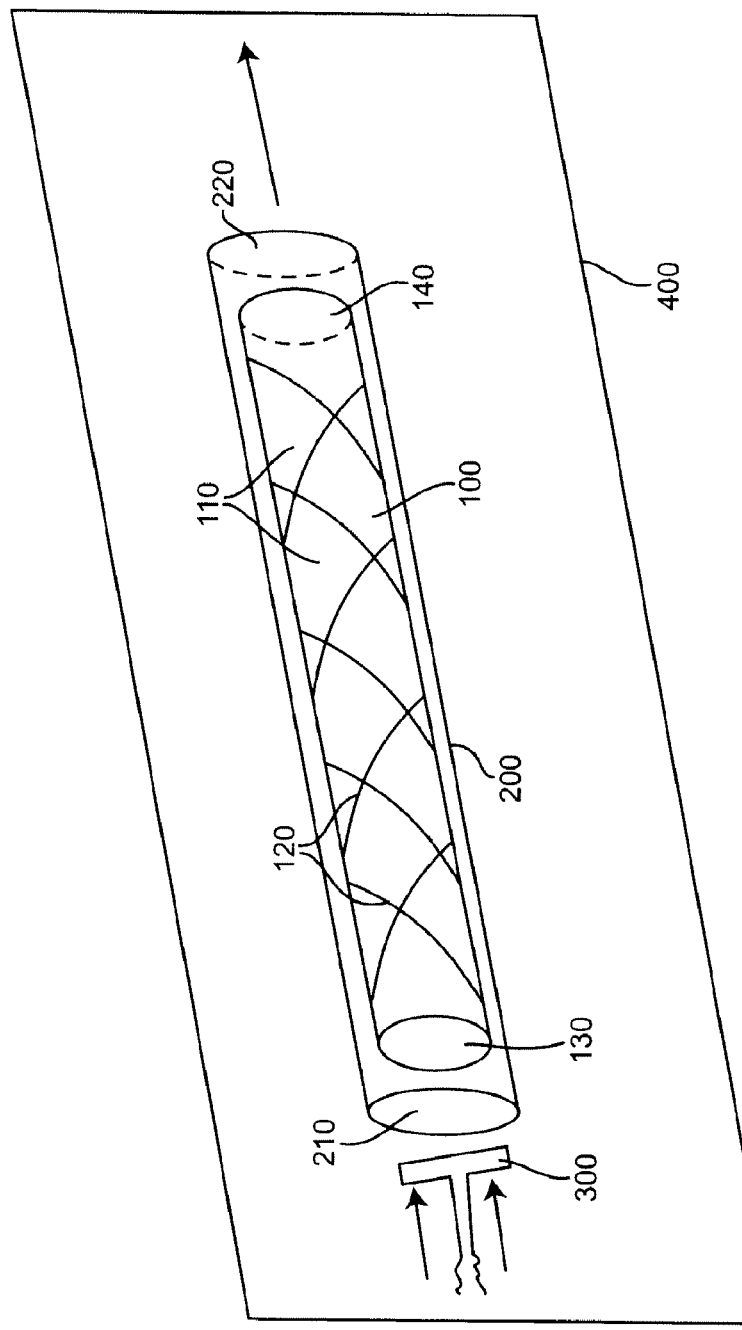
Figure 4E:
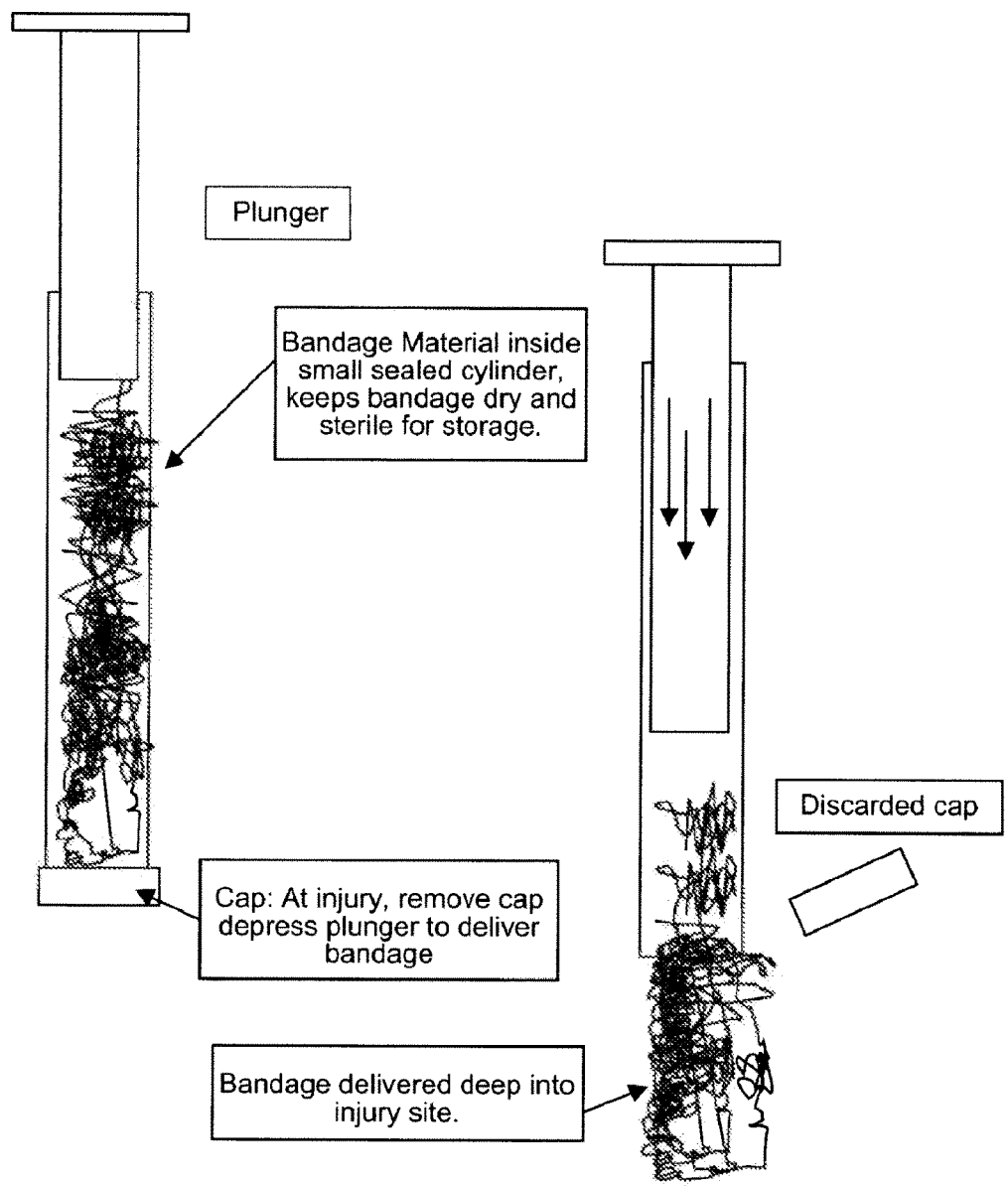

An exemplary schematic depiction of this embodiment of the invention is provided in FIG. 4D, where device 100, comprised of spun dextran fibers 110 and (optional) support material 120, and having a first end 130 and second end 140 is illustrated as enclosed within tube 200. Device 100 is enclosed within tube 200 but is not shown in phantom for the sake of clarity. Tube 200 has openings 210 and 220, both of which may be capped prior to use (caps not shown) or may be left open, especially if the entire apparatus is packaged in sterile packaging 400. Sterile packaging 400 is removed or breached to provide access the apparatus prior to use. In order to use the apparatus, openings 210 and 220 of the tube must be open. To deliver device 10 to a penetrating wound, an object such as plunger 300 in inserted into end 210 of the tube. Pressure is exerted on device 100 as plunger 300 contacts device end 130, and device 100 is consequently pushed out of tube 200 via opening 220 (in the direction indicated by the arrows) and into the penetrating wound (not shown). A second schematic representation of such a device is provided in FIG. 4E. In this depiction, support material is not included and the dry, sterile bandage material (e.g. dextran fibers) with associated therapeutic agents is located or positioned within a small, sealed cylinder with a cap at one end and a plunger at the other. Upon deployment, the cap is discarded, the open end of the cylinder is placed over the mouth of the wound and may be inserted into the wound, and the plunger is depressed, displacing or injecting the bandage material deeply into the wound. Similar designs may be used to deliver the device of the invention to orifices or channels such as the nasal passages, the ear canal, the vagina, the anus, into blood vessels, etc. The dextran fibers that are used in such an application will be formed into a device that is on the order of about 1 to about 6 inches in length, and from about ¼ inch to 1 inch in diameter, i.e. the dimensions will be suitable for insertion through the external opening and deep into an orifice or a wound cavity.

All such arrangements, shapes, and embodiments of EDF layers and support materials as described herein are intended to be encompassed by the invention.

The devices of the invention may be sterilized prior to use, generally by using electromagnetic radiation, for example, X-rays, gamma rays, ultraviolet light, etc. If thrombin is included in the device, the moisture content of the device (e.g. a bandage) should be reduced to 5% or less, in order to preserve thrombin activity during sterilization. This can be achieved by drying the fabricated bandage, e.g., under a vacuum, or by using a fabrication method that reduces moisture content from the beginning. Typically, the EDF devices of the invention are sterilized using X-rays in a dose of about 5 kilograys (kGray). Any method that does not destroy the dextran fibers or the activity of substances associated with the fibers, may be used to sterilize the devices of the invention.

When the device of the invention is a bandage, the substances of interest that are associated with the fibers of the bandage may include thrombin and fibrinogen, and the bandage may be used to staunch bleeding. However, the range of active ingredients may vary with the specific application of the bandage. For example, bandages comprised of only dextran or only thrombin might be used for small injuries or in combination with other interventions. In addition, other therapeutically beneficial substances may also be associated with the bandage, including but not limited to: antibiotics, medicaments that alleviate pain, growth factors, vasoactive materials (e.g. substances that cause vasospasms), steroids to reduce inflammation, etc. In other embodiments, the devices of the invention need not comprise agents that promote clotting at all. Those of skill in the art will recognize that the devices of the invention are highly suitable for delivering many substances of interest to a desired liquid environment or location. For example, the devices may be designed for delivery of therapeutic or beneficial substances to any moist environment of the body, where there is sufficient liquid to dissolve the EDFs and release the active substance, and where dissolved dextran is not problematic. Examples include but are not limited to oral, nasal, tracheal, anal, lung, and vaginal delivery of substances such as anti-microbial agents, analgesic agents, nutritional agents, etc. Oral applications include the delivery of substances useful for dental treatments, e.g. antibiotics, pain medications, whitening agents, etc. Further, the devices of the invention may be ingested to provide a quick release into the gastrointestinal tract of substances such as nutritional supplements (vitamins, amino acids, sugars, etc.). At the site of delivery, usually a bodily fluid is or will be present, and the dextran fibers dissolve in the fluid, thereby releasing or delivering the associated active agents or interest to the site. Such bodily fluids include fluids that are excreted or secreted from the body as well as fluids that normally are not, examples of which include but are not limited to blood, sweat, tears, mucus (including nasal drainage and phlegm), pleural fluid, pus or other wound exudates, saliva, vaginal secretions, and the like. However, in some embodiments, no bodily fluid is present (or if insufficient body fluid is present) and the applied device can be "activated" by wetting, e.g. by spraying, or by otherwise applying a source of moisture (e.g. by exposing the device to a moist material such as a sponge), or dropping devices into a liquid (e.g. a body of water), in order to cause release of the agents of interest associated with the dextran fibers. This embodiment of the invention may be especially useful, for example, for the release of materials at a site of interest, when activation is desired to occur only upon exposure to liquid. Examples include but are not limited to: delivering nutrients, fertilizers, insecticides, etc. to plants or grass using sheets of dextran fibers; the application of cosmetics; etc. The agents of interest may be relatively innocuous (benign) materials for which maintenance or storage in a dry state until use is desired; or they may be dangerous or toxic materials which must be kept sequestered and in a dry state until use. The devices of the invention are thus not limited to therapeutic treatments. Any substance of interest that can be dried sufficiently so as not to dissolve the EDFs prematurely (before placement at a location of interest) and which retain activity upon rehydration when delivered to a location of interest, may be delivered by the methods and devices of the present invention.

Due to the small footprint and light-weight characteristics of the devices of the invention, they are ideal for situations where space and weight of supplies are at a premium. Examples of such situations include but are not limited to: military operations where the weight and size of the components of a soldier's gear are an issue; in first aid kits; for emergency care during travel (e.g. during space flight, camping, etc.); etc. However, this need not always be the case. The devices may be used in a variety of situations and for a variety of purposes in which space and weight are not considerations. For example, the bandages of the invention provide a convenient means to administer thrombin and fibrinogen to surgical wounds in a conventional operating theater. The devices of the invention may also be advantageously utilized whenever it is desired to package and eventually release one or more dried substances, but where it is unfeasible or undesirable to handle the dried substances directly, e.g. where the quantity is extremely small, or the substance is toxic. In such cases, the EDF devices of the invention may serve as a "scaffolding" or carrier for containing, storing and/or transporting the substance(s) until use, i.e. until contacted with liquid that dissolves the EDFs, concomitantly releasing the substances into the liquid. Such substances may include, for example, enzymes or their precursors (e.g. pro-enzymes or zymogens) and their substrates, substances that activate a protein or enzyme (e.g. proteases, cofactors, etc.), and the like.

EXAMPLES

Example 1: Bandage Fabrication

Approximately 5 g of dextran (100,000-200,000 Mr) was used to produce a bandage that has a total weight of about 7 g after the addition of 2 gms of particulate fibrinogen. Approximately 5 g of dextran was suspended in distilled water at a concentration of 1.0 gm/ml. This solution was incubated overnight on a clinical rotator set to rotate 1-5 rotations per minute. These conditions were used to insure that the dextran is completely in solution. The dextran solution was loaded into a syringe capped with a blunt tipped needle, and approximately 5 mls per bandage was used in the fabrication process. For electrospinning, the syringe was mounted into a syringe driver calibrated to deliver 3-5 mls/hour to the electric field. The syringe driver is used to meter the delivery of material to the electric field and this setting does not necessarily accurately reflect the rate of fabrication as the electric field draws the dextran from the syringe.

Salmon fibrinogen was supplied by Sea Run Holdings (Evelyn Sawyer, Freeport Me.) and 1.5-2.0 g of fibrinogen was used per bandage. Salmon thrombin was supplied by Sea Run Holdings (Evelyn Sawyer, Freeport Me.) and 4500 units of thrombin activity was used per bandage. Salmon fibrinogen is supplied by Sea Run Holdings as a dry powder. The raw material was removed and processed into a very fine powder with a mortar and pestle. Approximately 1.5-2.0 gm of fibrinogen is used per bandage. Salmon thrombin is provided by Sea Run Holdings in a similar physical state (a dry powder). The thrombin was added to the fibrinogen and processed into a fine powder. The well blended, dry fibrinogen and dry thrombin mixture were placed into a salt shaker or other sifting device.

For electrospinning, two separate, high voltage power supplies were used to process the dextran into a fibrous matrix. The positive pole of one power source was attached to the syringe reservoir containing the dextran using an alligator clip. The negative pole of the second power source was attached to the ground target. A flat sheet of steel about 5×5 inches is typically used as a target. A piece of paper was placed over the target, and 1 micron diameter fibers of dextran accumulated on the paper during electroprocessing. The final product was easily removed from the paper. One of skill in the art of electrospinning will recognize that it is possible to switch the polarity of the power supplies.

For electrospinning, the power supplies were set to approximately +20-25 kV (kilovolts) on the syringe containing the dextran solution and approximately −20-25 kV on the ground target. Electrospinning was conducted across an air gap that can vary from 12 in to 24 inches, and the syringe driver was set to deliver the dextran to the electric field at a rate of 3-5 mls/hr. Spinning was initiated and a suitable volume of material was collected on the ground target, perhaps 1 ml (or about 1 gm) of dextran was delivered to the target where it collected as a small flattened disk of material. The electric field was terminated at the ground target and an aliquot of fibrinogen and thrombin was shaken onto the forming dextran fibers.

Electrospinning was re-initiated until the fibrinogen/thrombin mixture was covered with fresh dextran fibers. The process was repeated until the bandage was completed. The delivery of small volumes/amounts of fibrinogen in frequent small aliquots of material was used to distribute the active ingredients throughout the bandage. It is also possible to layer the fibrinogen and thrombin into the forming bandage separately so as to separate the active components by a layer of dextran. The final product looks and feels very much like a cotton ball.

Example 2: Scaling of Electrospinning for Manufacturing

Electrospinning is a method of producing a fibrous matrix composed of small diameter, nano-to-micron scale fibers. This process can be scaled for manufacturing by at least 3 different methods:

Multiple Jets. The use of multiple jets represents a simple solution to scaling the manufacturing process. As depicted in FIG. 1, it is possible to use multiple jets to increase the throughput of electrospinning. This can be done with dextran, however, the humidity level of the processing environment must be controlled; excess moisture limits the volume of material that can be collected and small drops of overspray can cause the dextran to dissolve. The level of humidity should be controlled to be from about 30% to about 40%, and typically at least about 20%. In one embodiment, multiple jets are arrayed above a conveyor belt. Each jet delivers a set amount of dextran, the process stops, the belt may move forward to allow a dose of e.g. fibrinogen and/or thrombin to be added to each pile of dextran, the belt moves again, and electrospinning is re-initiated.

Electroaerosol. Dextran can be electro-aerosoled under pressure from a paint sprayer and or an air brush. Dextran and gas are delivered under pressure to the air brush. At the terminal portion of the air brush, the dextran solution is pushed into the air stream across a needle, forming a jet of material that is blown into the electric field. The process is driven largely by the pressure applied to the gas used to drive the reaction. This technique is very rapid, requiring approximately 10 minutes to produce a bandage-like volume of material. This is thus a very effective method of producing large amounts of material very quickly. If a room temperature air stream is used in the process, the tip of the electrospinning jet may dry and clog the spraying device. This can be managed by controlling the moisture content in the gas used to drive the aerosol. An electric field is not absolutely needed to form fibers when this method is used to process dextran. Fibers will form in the aerosol jet, and the jet appears to be dry enough to allow large amounts of material to collect quickly. The electric field does, however, aid in targeting the jet to a specific target. For example, a conveyor belt might be used to collect sheets of fibrous dextran. By charging the solution and the belt, the dextran can be effectively targeted to the desired collecting site. The ground target can be placed, for example, behind or under a conveyer belt. The ground does not have to be in direct contact with the dextran. Multiple jets could also be employed in this approach. By running multiple jets of aerosol onto a moving conveyer belt that is interspersed with "sifters" (to deliver the fibrinogen and thrombin), the powdered materials could be added sequentially in discreet layers to the forming bandage. Electrostatic Processing. Fabrication of dextran into fibers may be carried out using a "cotton candy machine". A cotton candy machine represents a cross between a true electrospinning device and an aerosol-like device. Moisture content in the forming fibers can be controlled by controlling the input temperature (and volume) of the air delivered to the fabrication chamber where the fibers are formed. An added advantage is that simple sugars can be processed in to fibers using this type of instrument.

Example 3: Electrospun Dextran for Use as a Backing

PGA and PLA (2 synthetic, biocompatible polymers) are used to provide strength to the backing material. Fibrinogen is added to the PGA/PLA mixture and clearly represents a protein element of the composition. A 90:10 mixture of hexafluoroisopropanol (HFP) is added to aqueous (water, culture media, PBS, etc.) solvent saturated with calcium chloride (the calcium helps to promote the clotting cascade, or other salt) solution is prepared. The PGA/PLA polymers and fibrinogen are added to this solution and allowed to go into solution. Typical conditions are 100 mgs of PGA/PLA mixture (ranging from 99:1.0 PGA/PLA to 1.0:99 PGA/PLA ratio), 10-50 mgs fibrinogen per ml of electrospinning solution. Once in solution, the composition is electrospun to form a fibrous mat of material. The synthetic polymers provide strength; the fibrinogen component provides cross-linkable sites for active ingredients to interact with during clot formation. Ideally the clot will form at the injury site as the active ingredients are released from the bandage, the clot will adhere to the wound bed, surrounding tissue and the backing of the bandage. The backing provides the structural support necessary to stabilize the wound bed. The backing and remnants of the bandage and clot may be surgically removed once the patient is stable and or transported.

Example 4: Determination of Immune and Inflammatory Response to Salmon Thrombin and Fibrinogen The goal of experiments carried out in this Example was to determine if salmon thrombin and fibrinogen would cause an adverse immune and inflammatory response and to examine the cellular basis for that response. We assessed the production of antibodies to the salmon components and determined if the coagulation activity of the swine was altered. We examined the histopathology to characterize the tissue response to salmon dressings in swine after excisional cutaneous surgery that created wounds with separated edges and found a lymphocyte response that included cellular proliferation and cytokine secretion. However, healing occurred normally and there were no signs of adverse immunological reactions to the dressings at the wound site.
Methods
Purification of Salmon Fibrinogen and Thrombin Salmon proteins were purified from salmon blood as previously described. [13] Briefly, salmon blood was drawn from 2-5 kg salmon and centrifuged to obtain plasma. The plasma was made 10 mM with benzamidine, 2 g/dL CaPO4 and 3 g/dL epsilon-aminocaproic acid. The plasma was passed over a gelatin-sepharose column to remove fibronectin. The fibrinogen was salt precipitated twice with ammonium sulfate in a method modified from Mosher and Blout (Mosher D F, Blout E R. J Biol Chem. 1973 Oct. 10; 248(19):6896-903). Salmon thrombin was purified from the CaPO4 pellet by the method of Michaud et al. (Michaud S E, Wang L Z, Korde N, Bucki R, Randhawa P K, Pastore J J, et al. Thromb Res. 2002 Sep. 1; 107(5):245-54). The pellet was dialyzed for 5 h against 20 mM Tris/HCl, pH 7.5, 0.15M NaCl, 1 mM EGTA and 0.1M EDTA and then overnight against the same buffer without EDTA. The resulting protein solution was then subjected to two rounds of ammonium sulfate precipitation, first with 35% and the second time with 70% ammonium sulfate. The resulting pellet containing prothrombin was dialyzed against 20 mM Tris/HCl 1 mM EGTA for 5 h and then against 20 mM Tris/HCl 1 mM EGTA and 0.1 M NaCl. Finally, the solution was centrifuged at 12,000×g to remove contaminating particles. Fibrinogen was used at a concentration of 19.4 mg/cm$^2$ (2000 mg total) and thrombin was used at a concentration of 50 U/cm$^2$ (5200 U total).
Electrophoresis, Western Blotting and ELISA Immunological reactivity was determined by Western blotting and ELISA. For electrophoresis, proteins were dissolved in 4× sample buffer (Invitrogen Corp., Carlsbad, Calif.), heated to 80° C. and separated for 45 minutes at 200V on Invitrogen NuPAGE 4-12% Tris-Bis gels. Proteins were transferred from the gels to PVDF membranes and the membranes were blocked in Tris-saline, 5% dry milk for 1 hour. Following blocking, the membranes were incubated with porcine serum diluted 1/10 in Tris-saline buffer, with 4% bovine serum albumin. Antibody reaction was visualized after incubation with secondary anti-swine horse radish peroxidase-conjugated antibody (HRP-swAB) and treatment with Millipore Chemoluminescence reagent kit.

ELISAs were performed with thrombin or fibrinogen as the substrate. Immunolon B1 plates were coated with 1 µg protein/well, the wells were blocked and then incubated with porcine serum at 1/10 dilution. Titration curves were performed at dilutions up to 1/5000. Antibody binding to salmon proteins was quantified by incubation with horse radish peroxidase (HRP)-swAB and Millipore substrate and read at OD450 with a Molecular Devices plate reader.

Cytokine levels for IL1, IL2, IL4, IL6, IL8, IL10, IL12p40, IFNγ and TNFα were assayed by a commercial service, Searchlight Cytokine Custom Multiplex Arrays, (Pierce Biotechnology, Inc., Rockford, Ill.). The Protoarray Human Protein Microarray, a 5000 protein array from Invitrogen Corp., was analyzed to screen the serum from five animals for the presence of anti-human antibodies generated following exposure of the swine to the salmon proteins This assay would detect antibodies recognizing proteins that are not included in the normal coagulation pathway and, therefore, may not be detected by our standard assays. Serum from blood taken at the time of surgery to implant the vascular access ports (VAP) was compared to serum taken at euthanization of the animals after the exposure to salmon proteins.
Surgical Preparation of Animals Female Yorkshire swine (*Sus scrofa Domestica*) (25-28 kg) were prepared for surgery and monitored during the procedure as described previously. A vascular access port (VAP) catheter line (Access Technologies, Skokie, Ill.) was inserted into the jugular vein using a modified Seldinger technique (Knebel P, Frohlich B, Knaebel H P, Kienle P, Luntz S, Buehler M W, et al. Trials. 2006; 7:20) to permit blood sampling. A 16-18-gauge, 2.5-3" introducer needle was inserted into the vein percutaneously, followed by a j-wire. An expander catheter was fed onto j-wire through the skin and into the jugular. The expander catheter was removed with the j-wire remaining in the jugular vein and a central venous catheter was fed onto the j-wire into jugular vein. The catheter was secured to subcutaneous tissues in a simple interrupted pattern with 3-0 PDS and the catheter was flushed with a citrate anticoagulant solution to verify placement into vein and to create a citrate lock. The catheter was then attached to the port, which was buried in a subcutaneous pocket on the shoulder.

Exposure to the salmon proteins was accomplished in several ways. In the first approach, thrombin and fibrinogen were injected intravenously through the vascular access ports. In the second method, paired identical full thickness dermal wounds were surgically created on the right and left dorsal skin surface, paramedial to the spinal column in four pigs and monitored for 7 days. A second group of four pigs were subjected to a similar pair of skin lesions and monitored for 28 days. The total number of wounds to evaluate in each time point was eight. For animals in the 7 day group, the right dorsal lesion was bandaged with a dressing composed of lyophilized fibrinogen produced by electrospinning the protein onto a rotating mandrel (Nanomatrix, Inc, Baton Rouge, La.). The dressings were applied to a full thickness dermal lesion approximately 2×2 cm. The left dorsal lesion was dressed with a commercially available, non-hemostatic bandage. For the 28-day animals, this was reversed and an electrospun dressing containing fibrinogen (500 mg) and thrombin (400 IU) was applied to the left side. Animals in the 28-day group were injected with thrombin (60 IU) and fibrinogen (200 µg) on day seven to simulate a re-exposure to the dressing. At the end of the time period, the animals in each group were euthanized and the carcass presented for necropsy.

For the third exposure method, a midline abdominal incision was performed and the fibrinogen/thrombin bandage was inserted into the peritoneal cavity. The incision was sutured and the animal was recovered. Animals were maintained for two weeks and blood was drawn for analysis of antibody generation.

Tissue Preparation for Histological Examination

At necropsy, each pig was placed in lateral recumbency and the skin defects measured, gross lesions noted and recorded, and photographs were taken. The tissue of the salmon fibrinogen/thrombin treated and non-hemostatic bandage treated lesions, the pre-femoral lymph nodes, mesenteric lymph nodes and spleen were harvested for histopathology. The tissue samples were fixed in 10% neutral buffered formalin and then routinely trimmed, processed, and embedded in paraffin wax for sectioning and staining. Histopathology assessment was performed in a non-blinded fashion using a light microscope. Evaluation parameters on the skin sections included comparison of the wound edge with the wound center of the salmon fibrinogen/thrombin bandage treatment versus the non-hemostatic bandage treatment for signs of inflammation, re-epithelialization, granulation tissue, fibrosis, crust formation and necrosis. Semi-quantitative scoring of the skin samples for superficial and deep inflammation was performed, based on the amount of inflammatory response evident on standard H&E stained tissue sections. The scale was (1) minimal, (2) mild, (3) moderate, and (4) marked (data not shown). The mesenteric lymph node, pre-femoral lymph nodes and spleen from each animal were also evaluated for histopathology.

Statistical Analysis

Differences between groups were analyzed using a two tailed T-test assuming equal variances. Values are expressed as means±the standard error. N values and p values are included with each measurement.

Results

Inflammation and Re-Epithelialization of the Skin Lesion in the 7-Day Group

Paired dermal injuries were produced on the animals and the injury sites were dressed on one side with the salmon fibrinogen dressing and on the other with a non-fibrinogen standard dressing. After 7 days, the animals were euthanized and taken for necropsy ("7-day group"). In the center of the wound, all four pigs on both the left and right sides, exhibited a leading edge of epithelial cells and superficial wound filling by a coagulum composed of necrotic cellular debris, neutrophils, fibrin, hemorrhage, and edema.

Inflammatory cells, granulation tissue and edema expanded the superficial dermis on both the left and right sides subjacent to this fibrinonecrotic coagulum. Histologically, this granulation tissue was composed of many small caliber blood vessels lined by hypertrophied endothelium and oriented perpendicular to the skin surface. The edema separated the dermal collagen bundles and fibroblasts. Evidence of fibroplasia, characterized by numerous plump, activated fibroblasts with deposition of abundant collagen, extended from the junction of the dermis deep to the panniculus adiposus. This fibroplasia was moderate in severity with a multifocal to diffuse distribution in all four pigs on both the right and left sides.

Superficial inflammation of all eight wounds was moderate to marked in severity and composed of primarily neutrophils, fewer macrophages and rare multinucleate inflammatory giant cells subjacent to the fibrinonecrotic scab. Deep inflammation was marked in one salmon fibrinogen/thrombin treated lesion, and mild to moderate in the remaining right side lesions. Deep inflammation in the non-hemostatic treated lesions was marked in two cases and mild to moderate in two cases.

An attempt at re-epithelialization on the wound edges was evident in all eight wounds at the 7-day time point. Typical findings at these margins included epidermal hyperplasia, acanthosis, spongiosis, deep rete ridges and dermal pegs, parakeratotic hyperkeratosis and projections of regenerative epithelial cells toward the wound center.

To summarize the 7-day group, all wounds were filled with a fibrinonecrotic coagulum. Each wound exhibited superficial granulation tissue in the dermis on both the treated and untreated sides. There were numerous neutrophils, fewer macrophages and multifocal hemorrhage. Inflammation variably extended deep into the subcutis and was composed of lymphocytes, plasma cells and macrophages. Re-epithelialization at the margins and moderate fibroplasia was evident in all eight wounds. It is noted that the addition of other active materials such as growth factors or collagen, as described herein, may be of help in reducing inflammation and promotion healing.

Inflammation and Re-Epithelialization of the Skin Lesion in the 28-Day Group

To fully investigate the healing process, the dermal injuries were repeated in a second set of animals and the course of healing was followed for at least 28 days ("28-day group"). In this 28-day group, seven of eight wounds exhibited complete re-epithelialization that was characterized by epidermal hyperplasia and hyperkeratosis and multifocally there was a superficial clot similar in cellular composition to the 7-day group. In these seven wounds, the superficial inflammation was minimal to mild. One non-hemostatic bandage treated wound in the 28-day group displayed incomplete re-epithelialization and the wound defect was filled by a fibrinonecrotic coagulum along with marked superficial inflammation. The wound edge in this case exhibited similar epithelial cell hyperplastic changes as the 7-day group. All eight wounds exhibited mild amounts of dermal granulation tissue and deep inflammation that was composed of perivascular lymphocytes and macrophages.

Fibroplasia and collagen deposition was brisk in comparison to the 7-day group. This change extended from the junction of the dermis to the subcutaneous fat in all eight wounds.

Superficial inflammation was minimal to mild in the four non-hemostatic bandage treated lesions and generally composed of few lymphocytes, plasma cells and macrophages. Superficial inflammation in the salmon fibrinogen/thrombin bandage treated side varied from minimal in one case, mild in two cases and marked in one case. The minimal to mild cellular infiltrate was similar to the non-hemostatic bandage treated wounds. However, the one marked case of inflammation in one wound on the salmon fibrinogen/thrombin bandage side was composed of numerous neutrophils with fewer dermal macrophages, lymphocytes, plasma cells and eosinophils. Neutrophils rarely formed intra-epidermal pustules. Additionally, there was hemorrhage, fibrin and edema with necrosis in this wound.

Deep inflammation in the non-hemostatic bandage treatment varied from minimal to mild in three cases and moderate in one case. This subacute inflammation was predominantly clustered around vessels. In the salmon fibrinogen/thrombin treatment, deep inflammation was minimal in two cases and moderate in two cases; subacute and primarily perivascular.

In summary, the 28-day group exhibited complete re-epithelialization in seven wounds, which was covered by a fibrinonecrotic scab. Granulation tissue was evident in the superficial dermis. The inflammation was primarily composed of mononuclear cells. Fibroplasia was abundant. One wound treated with the salmon fibrinogen/thrombin dressing exhibited similar histopathology lesions as the 7-day group, including incomplete re-epithelialization and marked inflammation.

Immune Organ Involvement

The lymph nodes and the spleen were histologically examined for signs of activation, including lymphoid follicle formation and lymphocytolysis. The mesenteric lymph nodes and spleen were found to be similar histologically among the four pigs in each time point. The amount of white pulp (lymphoid tissue containing T and B lymphocytes) contained in the spleen increased slightly in the 28-day samples compared to the 7-day samples.

Although mesenteric lymph nodes showed little difference between the 7-day and 28-day groups, the pre-femoral lymph nodes that drain the ipsilateral area of the skin wound did display differences when examined at the 7-day time point. The node draining the non-hemostatic bandage wound generally exhibited fewer and smaller lymphoid follicles and decreased turnover of lymphoid cells than the pre-femoral nodes that drained the salmon fibrinogen/thrombin wound. By the 28-day time point, lymph nodes from both sides showed equivalent size of germinal centers and amount of lymphocytolysis.

Systemic Changes in the Immune Status as Determined by Cytokine Levels

Figure 5B:
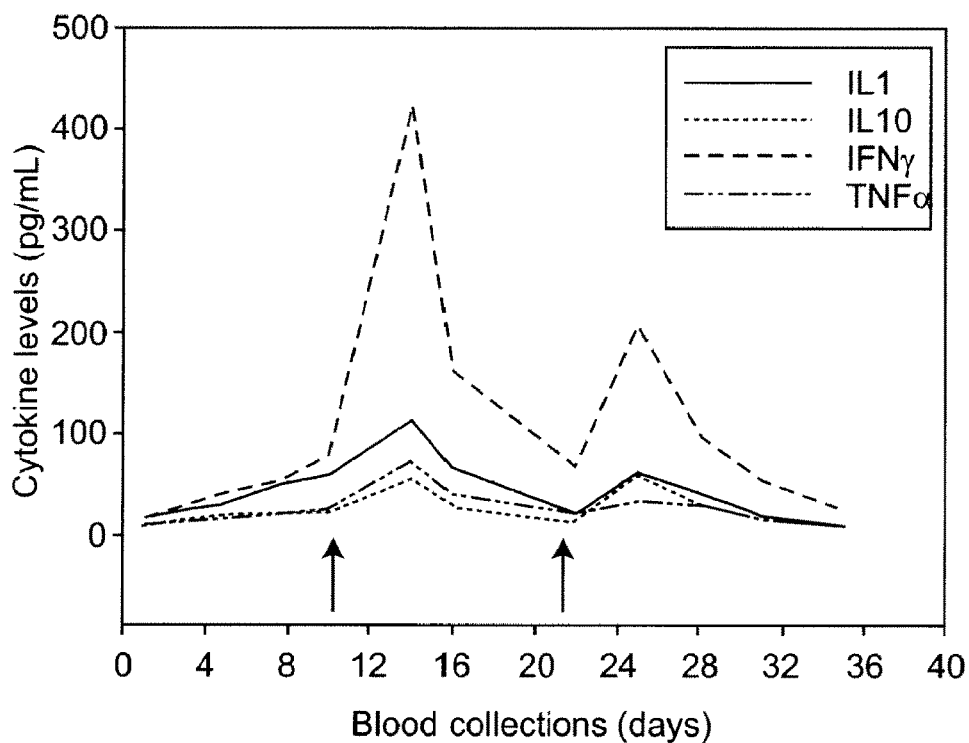
Figure 7A:
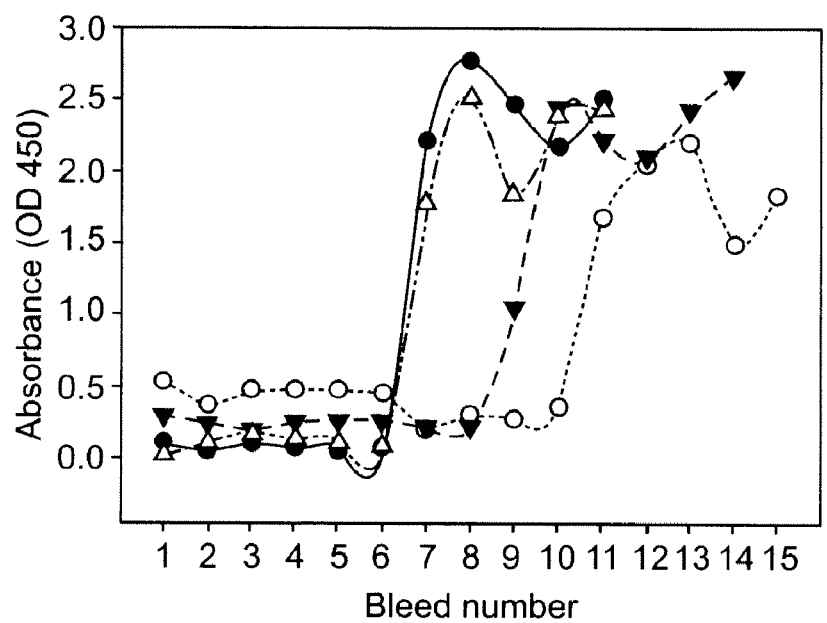
Figure 7B:
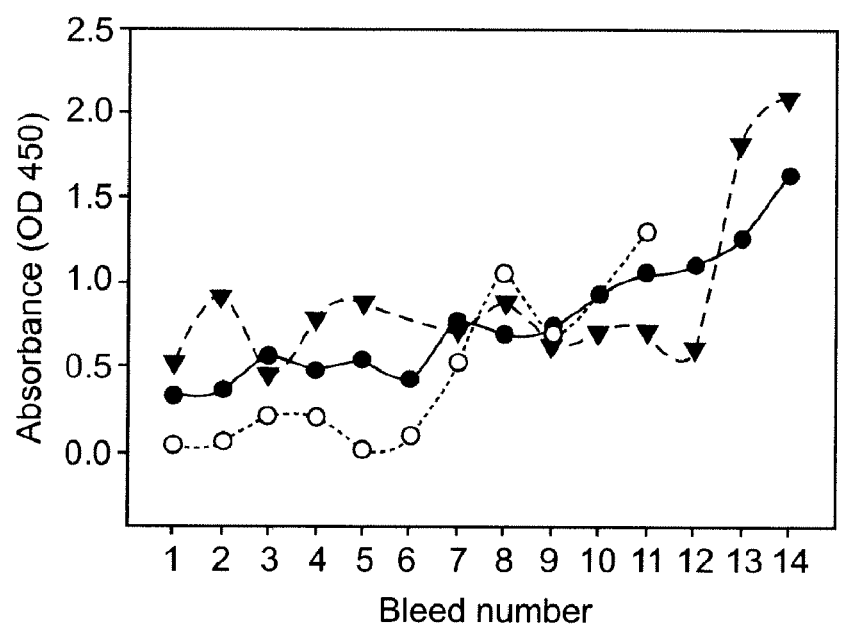
Figure 7C:
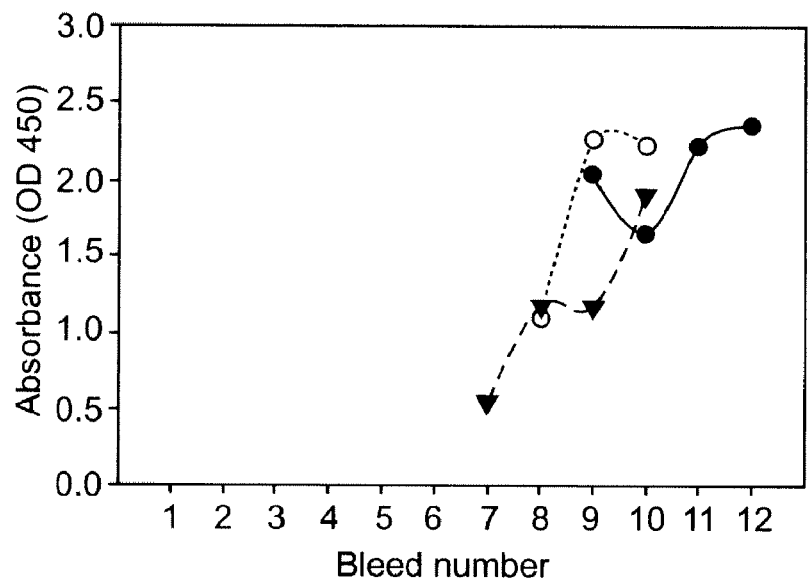
Figure 7D:
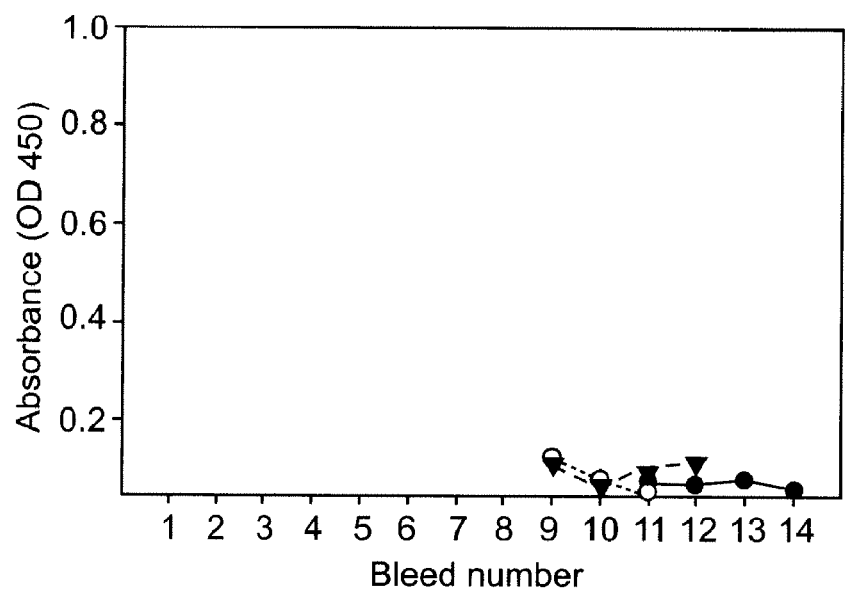
Figure 8A:
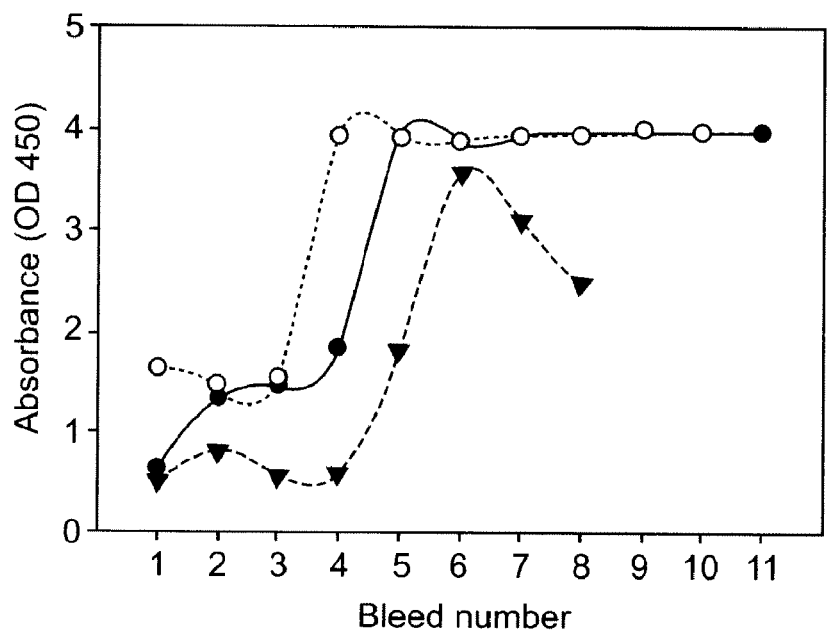
Figure 8B:
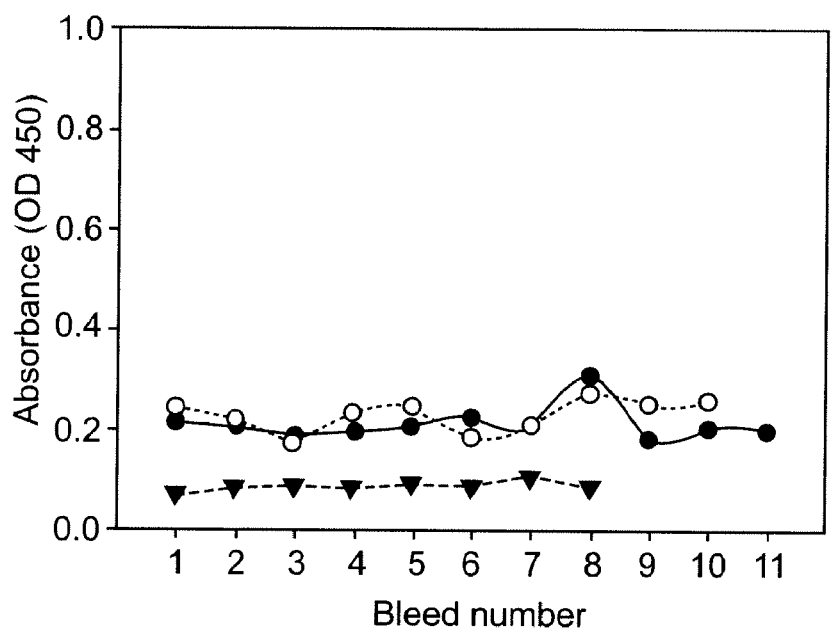
Figure 8C:
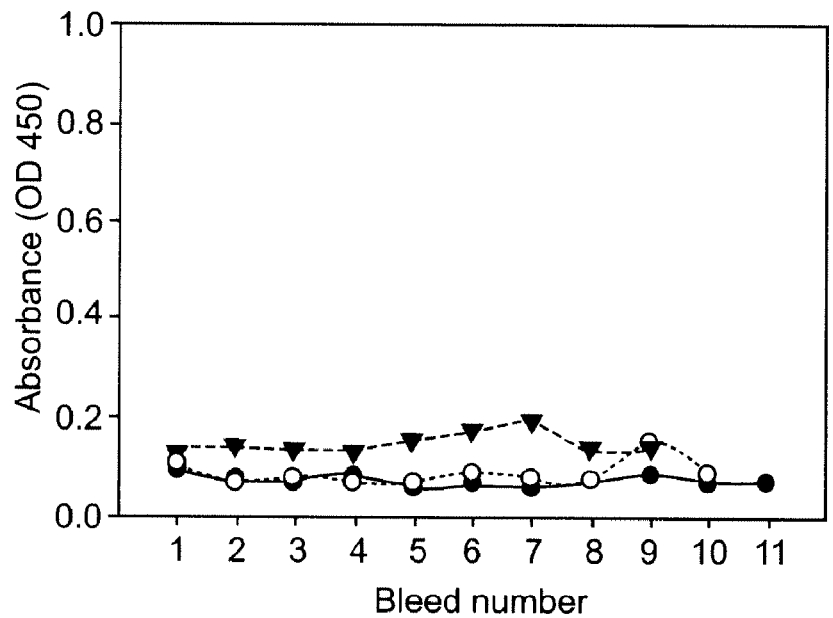
Figure 8D:
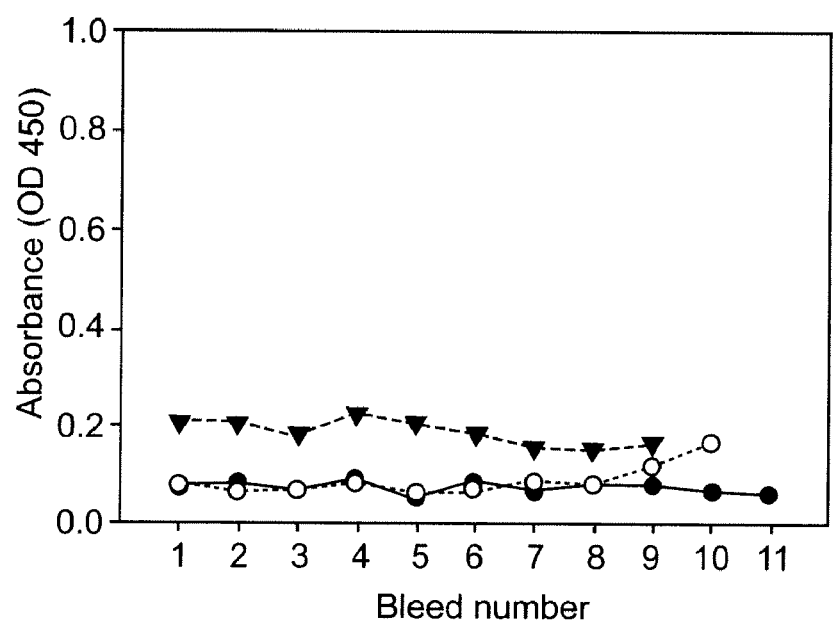
Figure 9A:
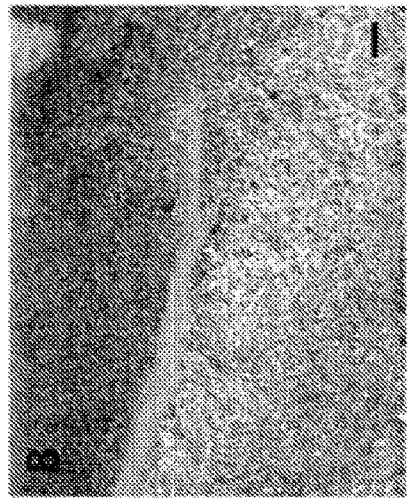
Figure 9B:
Figure 9C:
Figure 9D:

To determine if the morphological changes observed in the lymph nodes and the spleen were reflected in the systemic circulation of immunomodulatory or inflammatory signaling molecules, levels of a panel of cytokines were measured in the groups of animals exposed to the dermal wound and then intravenously infused two weeks later with soluble salmon proteins. Levels of IL-1β, IL-6, TNF-α, IFN-γ, IL-4 and IL-10 are shown in FIG. 5A as the log ratio of the cytokine level determined in blood drawn at the initial surgery to implant the vascular port compared to levels following exposure. Responses varied between individual animals from almost no response to 20-30-fold increases. Changes were seen in both pro-inflammatory responses (IL-1β, IL-6, TNF-α, IFN-γ) and humoral responses (IL-4 and IL-10). Changes in the cytokines within an individual animal are shown in FIG. 5B where it can be seen that initial exposure and the subsequent infusion of proteins elicited a response that could be detected in samples taken at the next blood drawn.

Characterization of Antibody Production in Treated Animals Against Thrombin and Fibrinogen Blood drawn from animals (n=24) that had been exposed to salmon thrombin and fibrinogen was analyzed for the generation of antibodies using Western blotting and ELISA. Sera of animals exposed to salmon protein by the dermal protocol and the abdominal were assessed for the production of antibodies as described in FIGS. 6A-F. Serum with detectable antibodies (+), undetectable antibodies (−) and serum not assayed (NA) are listed in Table 1, where "Abd" is abdomen. If antibodies were detectable as binding to any fibrinogen subunit or thrombin or prothrombin, that serum was counted as positive. The majority of animals (94%, see Table 1) that were exposed to salmon proteins generated antibodies that recognized salmon fibrinogen (FIG. 6) and 66% of the animals developed antibodies that reacted with human fibrinogen. In contrast, thrombin antibodies were low or undetectable after one exposure but were detectable at low titers (1/10) after a second exposure (FIG. 6) in some animals (4/24). These antibodies varied in that some only recognized the prothrombin form while others recognized the cleaved thrombin molecule. Isotypes of IgM and IgG were detected for both antigens, but IgA antibodies were not detected by either Western Blotting or ELISA.

TABLE 1

Antibody response in swine exposed to salmon fibrinogen/thrombin dressing as accessed by Western blotting.

| Animal number | Procedure | Salmon FIB | Human FIB | Swine FIB | Salmon THR | Human THR | Swine THR |
|---|---|---|---|---|---|---|---|
| 12171 | skin patch | | | | | | |
| 12172 | skin patch | + | − | +* | − | − | − |
| 12173 | skin patch | + | − | +* | − | − | − |
| 12174 | skin patch | + | + | +* | − | − | − |
| 13085 | Abd patch | + | + | +* | − | + | + |
| 13086 | Abd patch | + | + | +* | − | − | − |
| 13087 | Abd patch | ** | | | | | |
| 13088 | Abd patch | + | + | +* | + | + | − |
| 14029 | Abd patch † | + | + | | | | |
| 14031 | Abd patch | + | + | | − | − | − |
| 14032 | Abd patch | | | | | | |
| 14033 | Abd patch | | | | | | |
| 14871 | Abd patch | + | − | + | − | − | − |
| 14872 | Abd patch | + | − | + | − | − | − |
| 14873 | Abd patch | | | | | | |
| 14874 | Abd patch | − | − | + | − | − | − |
| 16954 | Abd patch | + | − | + | − | − | − |
| 16955 | Abd patch | + | + | + | − | − | − |
| 16956 | Abd patch | + | + | + | − | − | − |
| 16957 | Abd patch | + | + | + | − | − | − |
| 17218 | Abd patch | + | + | | + | − | |
| 17219 | Abd patch | + | + | | + | + | + |
| 17220 | Abd patch | + | + | | + | + | + |
| 17222 | Abd patch | + | + | + | + | + | + |

The time course of antibody development was determined by ELISA on sequential blood samples taken from two series of pigs, one set subjected to the skin lesion animals and one set that received the abdominal patch placement. The results were plotted as optical density vs. blood collection time, starting with blood collected at the implantation of the VAP until the termination of the experiment. Animals that were exposed to the bandage via the skin lesion modality (FIG. 7A-C) displayed slightly different responses compared to animals that were exposed via the abdominal placement of the patch (FIG. 8A-D). Animals that were in the abdominal patch group had very low responses to human fibrinogen and low responses to both salmon thrombin and human thrombin. The blots in general proved to be more sensitive in detecting very low levels of responses to the protein, but the ELISAs enabled us to easily track the progression of the immune response and antibody production in each animal.

Identification of Human Cross-Reactive Antibodies in the Serum of Salmon Protein-Exposed Swine The Protoarray Human Protein Microarray service from Invitrogen Corp. was utilized to screen the serum from five animals that had been exposed to the salmon proteins for the presence of antibodies reactive against human proteins generated following exposure of the swine to the salmon proteins by either the skin and abdomen placement. These proteins could fall into two categories, 1) proteins that were part of the coagulation cascade and whose function could possibly be inhibited by interfering antibodies or 2) proteins that have no perceived relationship to the coagulation process, but may still react with antibodies induced during exposure. Sera from animals was assayed by Invitrogen for reactivity to a microarray displaying 5000 proteins to determine if antibodies were being generated in the treated swine that may recognize human protein that were not assayed by Western blotting. As shown in Table 2, the array had 4 proteins that were part of the coagulation cascade and 5 that were related to transglutaminase (Factor XIII) activity or were coagulated related. All 5 of the animals tested had strong initial reactions against the human transglutaminase 2, but none showed an increase following exposure and none of the animals had impaired coagulation responses (see below). Most antibodies to coagulation proteins did not show significant changes pre- to post exposure in this assay system. A second group of proteins is also presented in Table 2. These are proteins that showed significant increases in antibody responses following exposure of the animals to the salmon proteins, but are not related to the coagulation process. There were 15 non-coagulation proteins showing increased reactivity to antibodies following exposure to the salmon proteins that fell into this class with a p-value threshold (initial vs final value) of <0.05.

TABLE 2

Screening of human protein-swine antibody interactions with the Invitrogen ProtoArray 5000 protein microarray.

| Factor | Common name | Related ProtoArray Content | Signal level (arbitrary units*) Pre | Signal level (arbitrary units*) Post |
|---|---|---|---|---|
| Coagulation or coagulation-related proteins contained on the ProtoArray 5000 | | | | |
| I | Fibrinogen | fibrinogen-like 1, transcript variant 1 | 0.5 | 0.5 |
| II | Prothrombin | serine (or cysteine) proteinase inhibitor, clade C (antithrombin), member 1 | 0.5 | 0.5 |
| III | Tissue factor, tissue thromboplastin | coagulation factor III (thromboplastin, tissue factor) (F3) | 0.5 | 0.5 |
| VIII | Antihemophilic factor A (globulin) (AHG) | coagulation factor VIII, procoagulant component (hemophilia A) (F8) | 0.5 | 0.5 |
| XIII | Protransglutaminase, fibrin stabilizing factor, fibrinoligase | see below | | |
| | Other coagulation related proteins | multiple coagulation factor deficiency 2 (MCFD2) | 0.5 | 0.5 |
| | Other coagulation related proteins | tissue factor pathway inhibitor (lipoprotein-associated coagulation inhibitor) | 0.5 | 0.5 |
| | Other coagulation related proteins | transglutaminase 2 (C polypeptide, protein-glutamine-gamma-glutamyltransferase), transcript variant 2 | 3-5 | 3-5 |
| | Other coagulation related proteins | transglutaminase 4 (prostate) transglutaminase 1 (K polypeptide | 0.1 | 0.1 |
| | Other coagulation related proteins | epidermal type I, protein-glutamine-gamma-glutamyltransferase) (TGM1) | 0.2 | 0.1 |
| | Other coagulation related proteins | CTL2114 TRANSGLUTAMINASE-known Autoantigen | 0.2 | 0.2 |
| | | ProtoArray Content | Pre | Post |
| Unrelated proteins contained on the ProtoArray 5000 showing reactivity | | | | |
| | | SUMO/sentrin specific protease, 8 | 0 | 4 |
| | | WW domain binding protein 2 (WBP2) | 1 | 5 |
| | | cellular retinoic acid binding protein 2 | 1 | 5 |
| | | RAB3A interacting protein-like 1 | 0 | 4 |
| | | nuclear factor I/A | 1 | 5 |
| | | secretogranin III | 1 | 5 |

TABLE 2-continued

Screening of human protein-swine antibody interactions with the Invitrogen ProtoArray 5000 protein microarray.

| | | |
|---|---|---|
| glycine-N-acyltransferase-like 2 | 0 | 5 |
| B-cell CLL/lymphoma 7C | 1 | 5 |
| phosphatidylinositol-4-phosphate 5-kinase | 0 | 4 |
| mahogunin, ring finger 1 | 1 | 5 |
| serpin peptidase inhibitor, 6 | 0 | 4 |
| ataxin 3 | 0 | 4 |
| Casein kinase 1, gamma 2 | 1 | 5 |
| Ribosomal protein S6 kinase | 0 | 4 |
| NIMA-related kinase 11 | 1 | 5 |

Discussion

Wound Healing in Animals Treated with Salmon Fibrinogen/Thrombin Dressings.

Because of the introduction of foreign proteins derived from the salmon blood into a wound site, we were concerned that the wound healing process may be impeded and that coagulopathy may be induced by initiation of an adverse immune response. To investigate these possibilities, we treated full thickness skin wounds with fibrinogen/thrombin dressings, control dressings, and compared the progress of wound healing and the state of activation of the lymph nodes and the spleen.

Excisional cutaneous wounds were surgically created in these eight pigs, bandaged with two different types of dressings, and monitored for two time points of seven or twenty-eight days following surgery. The 7-day and 28-day time points generally followed the well-established models of cutaneous wound healing by second intention where there are separated edges and no surgical opposition. Cutaneous wounds healed by second intention follow a complex process in closing the defect. These types of wounds display a robust, localized inflammatory response, form abundant granulation tissue and have a thin epidermis overlying scar tissue. As expected, the 28-day group exhibited complete re-epithelialization in seven out of eight wounds. Over time, these wounds would likely show some signs of scarring with contracture if allowed to progress for additional weeks and months.

A notable histopathology difference at the 7-day time point was increased activation of pre-femoral lymph nodes on the salmon fibrinogen/thrombin bandage treated side in contrast to nodes of the non-hemostatic treated side. This was not unexpected as it may reflect a greater degree of immune stimulation on the side exposed to the salmon protein bandages or it may be due to an increased coagulative response at the time of the initial wound, resulting from the fibrin/thrombin bandages.

The Immune Response of Swine Following Exposure to Salmon Fibrinogen/Thrombin Dressings Animals exposed to salmon fibrinogen/thrombin were monitored for health complications and blood was drawn to determine the immune response to the salmon proteins. The levels of the cytokines that were measured gave a good representation of the status of the response. The inflammatory cytokines (IL-1, IL-6, TNF-α and INF-γ) often mirrored the surgical manipulations while the humoral signals (IL-4 and IL-10) increased consistently with changes in the antibody titers. Our results show that the animals routinely made immunoglobulins to fibrinogen and, as expected, these were of the IgM and IgG classes. Furthermore, in most animals these antibodies recognized all three of the fibrinogen antigens that were assayed, salmon, swine and human fibrinogen. Thrombin, on the other hand, did not induce as universal response as fibrinogen did, with only 6 of the animals generating a thrombin response and only 4 of them producing antibodies that recognized swine thrombin. Titers of all of the antibodies were low and the Western blots were conducted with a high concentration of the serum (1/10 dilution) to permit visualization of the protein bands. There was some diversity in the antigens recognized by the antibodies with some of the antibodies only recognizing prothrombin and not thrombin, even though the prothrombin was a relatively small percentage of the sample.

Measurements of the coagulation parameters were conducted to determine if the antibodies inhibited the coagulation process, but all the measured values remained in the normal range. With the rationale that there may be hidden effects on human coagulation that was not detected in measurements of swine plasma clotting times, we mixed swine and human plasma together. In this experiment as well, we measured normal levels of coagulation. From a gross assessment of the animals' health as well as the biochemical assays described above, the antibodies did not seem to cause an adverse response.

Generation of Inhibitory Coagulation Factors in the Clinical Settings

Acquired coagulopathy is a rare but serious disorder that can arise when a patient generates antibodies that recognize and interfere with the normal function of components of the coagulation pathway. Antibodies have been reported to recognize and inhibit a range of coagulation proteins. Von Willebrand's disease is the most widely inherited blood disorder (Rodeghiero F, Castaman G, Dini E. Blood. 1987 February; 69 (2):454-9) and is most commonly due to low expression levels of functional VWF. However, it can also be caused by the inappropriate production of antibodies that can interfere with the von Willebrand polypeptide itself or the protease ADAMTS-13 (Shelat S G, Smith P, Ai J, Zheng X L. J Thromb Haemost. 2006 August; 4(8):1707-17) While the underlying cause for these autoantibodies may be due to immune dysfunction in the patient or a triggering health crisis that precipitates the autoimmune response, the use of coagulation agents in surgery as hemostatic agents has also been implicated as the cause of inhibitory antibodies that processes the polypeptide. Autoantibodies to Factors VIII or IX, although very rare, can lead to acquired hemophilia syndrome (Franchini M. Rituximab, Critical reviews in oncology/hematology. 2007 July; 63 (1):47-52). The use of bovine thrombin as a topical agent in all types of surgical procedures has been widespread with estimates of over a million uses in 2006. Reports have now documented adverse effects resulting from the antibodies developed against thrombin, prothrombin, factor V and cardiolipin following the use of these hemostatic agents. Many other cases of acquired coagulopathy are associated with surgery without specific reference to whether or not bovine thrombin had been used in those procedures. One approach to combat the autoimmune response has been to attempt to suppress the immune system and the drug rituximab, a monoclonal antibody directed at CD20, has proven to be effective in treating many case. A disadvantage of this treatment is the increased risk of leukemia and other cancers that occur when the host defense system is impaired. Clearly, any protein-based pro-coagulative therapeutic agent will need to prove that the risk of autoantibody induction and subsequent acquired coagulopathy is low. Our study has demonstrated that the immune system of pigs, while able to recognize the salmon proteins and generate antibodies, has not mounted a response that leads to coagulopathy and, in the short term, the animals remain healthy.

Example 5—Deployment of an Electrospun Dextran Bandage

Animals were generally prepped (anesthetized, instrumented for surgery) as described in Example 4. Briefly, a midline incision was performed to expose the abdominal aorta. This involves moving the large and small intestines to one side and cutting through the peritoneum to isolate the aorta. Aortic injury (4 mm punch) was performed and bleeding was permitted for 3-4 seconds. Thereafter, a bandage was applied with pressure for 4 min. Pressure was released and the injury was checked for hemostasis, and blood loss and physiological signs were measured. The experiment was terminated at 60 min or if mean arterial pressure fell below 20 mm Hg.
Results
Prior formulations of lyophilized bandages did not work well. For example, when thrombin and fibrinogen were lyophilized into the bandage, the bandage exhibited poor texture and 0/4 animals survived. Lyophilized bandages with added lipids resulted in 5/7 survival for 60 minutes. When a reduced amount of material was used to fabricate the bandages, 4/6 animals survived for 60 minutes.

Dextran bandages were first formulated with organic solvents and the bandages were very hard in texture, and did not dissolve well, and most animals (8/10 tested) died. The survival criteria was increased to 3 hours because we noted that some the animals listed as "surviving" at 60 min in previous experiments would not have lasted much longer. Importantly, in vitro tests of thrombin showed that the enzyme was inactive.

After bandage formulations were switched to use aqueous buffers, the bandages and results were much improved. Bandage texture was soft and pliable and the bandage could be folded and shaped to fit into the wound site. In vitro measurements of thrombin and clot strength showed great improvement. Thrombin was active and caused fibrinogen polymerization. Of the animals tested, 7/9 animals survived. During experiments, blood pressures would drop to mean arterial pressures of 30-50 mmHg and then recover to 50-70 mmHg. Heart rates typically increase to 160-180 bpm and eventually drop back to 120 bpm or lower after the wound stabilizes. Coagulation parameters remained normal over the three hours.

The effect of the bandages on the coagulation and healing process over time have also been examined for three different time periods: 1 week, 4 weeks and 6 months. These animals were not "injured" as described above but rather surgically exposed to the bandages. During each time period, all coagulation values were normal, all healing was normal (as tested by dermal wounds) and abdominally implanted bandages were absorbed without adverse effects. Necropsy showed minimal adhesion at the site of insertion. All animals made antibodies against salmon fibrinogen. These antibodies recognize human fibrinogen but not swine fibrinogen (self antigens). Antibodies were produced at low titers against salmon thrombin, but did not cross react with either human or swine thrombin.

FIGS. 9A-D show that wound healing that proceeds normally when treated with the bandage. Hematological parameters were measured to determine if antibodies developed following exposure to salmon proteins alter normal blood cellular composition or normal coagulation values. Mean, standard deviation and p values are presented in tabular form below, in Table 3A and B and Table 4. For Table 4, human plasma and swine plasma from 2 exposed animals were mixed and assayed for coagulation parameters to determine if there may be cryptic factors that could interfere with clotting. As can be seen, none of the parameters was significantly altered following exposure to the bandages of the invention.

TABLE 3A AND B

Changes in hematology and coagulation parameters before and after exposure to the salmon fibrinogen/thrombin dressing

A.

| | White Red Blood ($\times 10^9$/L) | | Red Blood Cells ($\times 10^{12}$/L) | | HCT (%) | | PLT ($\times 10^9$/L) | |
| --- | --- | --- | --- | --- | --- | --- | --- | --- |
| | initial | final | initial | final | initial | final | initial | final |
| Mean n = 30 | 19.88 | 17.30 | 5.79 | 5.98 | 29 | 30 | 444 | 426 |

TABLE 3A AND B-continued

Changes in hematology and coagulation parameters before and after exposure to the salmon fibrinogen/thrombin dressing

| | | | | | | | | |
|---|---|---|---|---|---|---|---|---|
| Standard Deviation | 3.96 | 3.10 | 0.43 | 0.50 | 3.23 | 2.74 | 89 | 126 |
| T-test p value | | 0.03 | | 0.24 | | 0.49 | | 0.62 |

B.

| | PT (sec) | | Activated partial thromboplastin time (APTT) (sec) | | Thrombin time (sec) | | Fibrinogen (mg/dL) | |
|---|---|---|---|---|---|---|---|---|
| | initial | final | initial | final | initial | final | initial | final |
| Mean n = 30 | 13.75 | 14.66 | 38.46 | 40.57 | 23 | 23 | 164 | 155 |
| Standard Deviation | 1.38 | 3.63 | 7.82 | 10.27 | 4.59 | 2.81 | 40.30 | 40.63 |
| T-test p value | | 0.32 | | 0.47 | | 0.83 | | 0.58 |

TABLE 4

Effects of immunized swine plasma on coagulation of human plasma

| Sample | Prothrombin time (sec) | Activated partial thromboplastin time (APTT) (sec) | Thrombin time (sec) | Fibrinogen concentration (mg/dL) |
|---|---|---|---|---|
| Swine A alone | 13.3 | 32.2 | 21.2 | 137 |
| Human alone | 13.0 | 29.5 | 16.7 | 313 |
| Swine A/Human 1:1 ratio | 11.9 | 26.5 | 22.2 | 215 |
| Swine B/Human 1:1 ratio | 11.8 | 26.7 | 21.2 | 206 |
| Swine A/Human 7:3 ratio | 12.2 | 34.0 | 23.3 | 179 |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A hemostatic product comprising:
    a first hemostatic layer comprising a first dextran support consisting of electrospun dextran fibers and thrombin placed on the first dextran support, and
    a second hemostatic layer comprising a second dextran support consisting of electrospun dextran fibers and fibrinogen placed on the second dextran support, wherein the first and second hemostatic layers are arranged in a stacked configuration to form the hemostatic product so that the thrombin is separate from the fibrinogen.

2. The hemostatic product of claim 1, and further comprising a top dextran support that covers the second hemostatic layer.

3. The hemostatic product of claim 1, wherein the hemostatic product comprises between about 5 and 10 of the first and second hemostatic layers.

4. The hemostatic product of claim 1, wherein the first dextran support has a moisture content of up to 5% by weight and wherein contact between the thrombin and the moisture causes the thrombin to be retained on the first dextran support.

5. The hemostatic product of claim 1, wherein the hemostatic product further comprises a support material selected from the group consisting of gauze, electrospun dextran, polyglycolytic acid polymers, polylactic acid polymers, caprolactone polymers and charged nylon and wherein the first hemostatic layer is adjacent the support material.

6. The hemostatic product of claim 1, wherein the thrombin is human thrombin and wherein the fibrinogen is human fibrinogen.

7. A method of preparing a hemostatic product according to claim 1 comprising:
    fabricating a first hemostatic layer by placing thrombin on a first dextran support that consists of electrospun dextran fibers;
    fabricating a second hemostatic layer by placing fibrinogen on a second dextran support that consists of electrospun dextran fibers; and
    arranging the first and second hemostatic layers in a stacked configuration so that the thrombin is separate from the fibrinogen.

8. The method of claim 7, and further comprising covering the second hemostatic layer with a top dextran support.

9. The method of claim 7, wherein the hemostatic product comprises between about 5 and 10 of the first and second hemostatic layers.

10. The method of claim 7, and further comprising placing the first hemostatic layer on a support material that is selected from the group consisting of gauze, electrospun dextran, polyglycolytic acid polymers, polylactic acid polymers, caprolactone polymers and charged nylon.

* * * * *